US010064543B2

(12) United States Patent
Motohara et al.

(10) Patent No.: US 10,064,543 B2
(45) Date of Patent: Sep. 4, 2018

(54) IMAGING UNIT, IMAGING MODULE, AND ENDOSCOPE SYSTEM HAVING A CIRCUIT BOARD WITH A RECESS

(71) Applicant: OLYMPUS CORPORATION, Tokyo (JP)

(72) Inventors: Hiroyuki Motohara, Hachioji (JP); Yasuhiro Kusano, Fukushima (JP)

(73) Assignee: OLYMPUS CORPORATION, Tokyo (JP)

( * ) Notice: Subject to any disclaimer, the term of this patent is extended or adjusted under 35 U.S.C. 154(b) by 46 days.

(21) Appl. No.: 15/414,731

(22) Filed: Jan. 25, 2017

(65) Prior Publication Data
US 2017/0127921 A1    May 11, 2017

Related U.S. Application Data

(63) Continuation of application No. PCT/JP2015/080964, filed on Nov. 2, 2015.

(30) Foreign Application Priority Data

Dec. 8, 2014 (JP) .................................. 2014-248300

(51) Int. Cl.
*A61B 1/05* (2006.01)
*H05K 1/18* (2006.01)
(Continued)

(52) U.S. Cl.
CPC .............. *A61B 1/04* (2013.01); *A61B 1/0051* (2013.01); *A61B 1/00114* (2013.01);
(Continued)

(58) Field of Classification Search
CPC ....... A61B 1/04; A61B 1/00114; A61B 1/051; A61B 1/05; H04N 2005/2255;
(Continued)

(56) References Cited

U.S. PATENT DOCUMENTS

| 7,649,740 B2 * | 1/2010 | Sekido ................... | H05K 1/144 361/735 |
| 7,876,573 B2 * | 1/2011 | Motohara .............. | H05K 1/144 361/770 |

(Continued)

FOREIGN PATENT DOCUMENTS

| EP | 2393345 A1 * | 12/2011 | ............. H05K 1/144 |
| JP | 2000-199863 A | 7/2000 | |

(Continued)

OTHER PUBLICATIONS

International Search Report dated Feb. 9, 2016 issued in PCT/JP2015/080964.

*Primary Examiner* — John P Leubecker
(74) *Attorney, Agent, or Firm* — Scully, Scott, Murphy & Presser, P.C.

(57) ABSTRACT

An imaging unit includes: a semiconductor package having an image sensor and having a connection electrode on a back side thereof; a circuit board having connection electrodes on front and back sides thereof, the connection electrode on the front side being connected to the connection electrode of the semiconductor package; a deformed circuit board having first, second, and third faces and having connection electrodes on the first, second, and third faces, respectively, a connection electrode on the first face being connected to the connection electrodes of the circuit board; an electronic component mounted on the back side of the circuit board; and cables connected to the connection electrodes on the second and third faces. The electronic component is housed in a recess of the deformed circuit board. The circuit board, the deformed circuit board, and the cables are located within a projection plane in an optical-axis-direction of the semiconductor package.

12 Claims, 21 Drawing Sheets

(51) Int. Cl.
*A61B 1/04* (2006.01)
*H04N 5/225* (2006.01)
*A61B 1/00* (2006.01)
*A61B 1/005* (2006.01)
*A61B 1/06* (2006.01)
*A61B 1/07* (2006.01)
*A61B 1/12* (2006.01)
*G02B 23/24* (2006.01)
*H05K 1/14* (2006.01)

(52) U.S. Cl.
CPC ...... *A61B 1/00124* (2013.01); *A61B 1/00165* (2013.01); *A61B 1/05* (2013.01); *A61B 1/0669* (2013.01); *A61B 1/07* (2013.01); *A61B 1/12* (2013.01); *A61B 1/127* (2013.01); *G02B 23/2484* (2013.01); *H04N 5/2257* (2013.01); *H04N 2005/2255* (2013.01); *H05K 1/144* (2013.01)

(58) Field of Classification Search
CPC ............ H04N 5/2257; H04N 5/2251; G02B 23/2484; H05K 1/144; H05K 2201/10515; H05K 5/0021; H05K 7/023; H05K 2201/042
See application file for complete search history.

(56) References Cited

U.S. PATENT DOCUMENTS 8,901,730 B2 * 12/2014 Liu ..................... H01L 23/488
                                                        257/698
2005/0260867 A1 * 11/2005 Ono ..................... H05K 1/144
                                                        439/65
2006/0109368 A1    5/2006 Ayrenschmalz
2007/0279890 A1   12/2007 Motohara et al.
2008/0170376 A1    7/2008 Sekido
2009/0021618 A1 *  1/2009 Schwarz ............. H04N 5/2251
                                                        348/294
2010/0033608 A1 *  2/2010 Chul .................... H04N 5/2253
                                                        348/294
2010/0284161 A1 * 11/2010 Motohara ........... H05K 1/0268
                                                        361/803
2011/0188210 A1 *  8/2011 Huang ..................... H05K 1/14
                                                        361/735
2012/0206583 A1 *  8/2012 Hoshi .................... A61B 1/042
                                                        348/76
2013/0258183 A1 * 10/2013 Kamei ................ H04N 5/2253
                                                        348/374
2014/0003018 A1    1/2014 Fujimori

FOREIGN PATENT DOCUMENTS

| JP | 2005-278760 A | 10/2005 |
| JP | 2006-174431 A | 6/2006 |
| JP | 2006-223624 A | 8/2006 |
| JP | 2007-318078 A | 12/2007 |
| JP | 2008-177295 A | 7/2008 |
| JP | 2011-200402 A | 10/2011 |
| JP | 2012-186301 A | 9/2012 |
| JP | 2012183330 * | 9/2012 ............ A61B 1/04 |
| JP | 2013-197501 A | 9/2013 |
| JP | 2014-110847 A | 6/2014 |

* cited by examiner

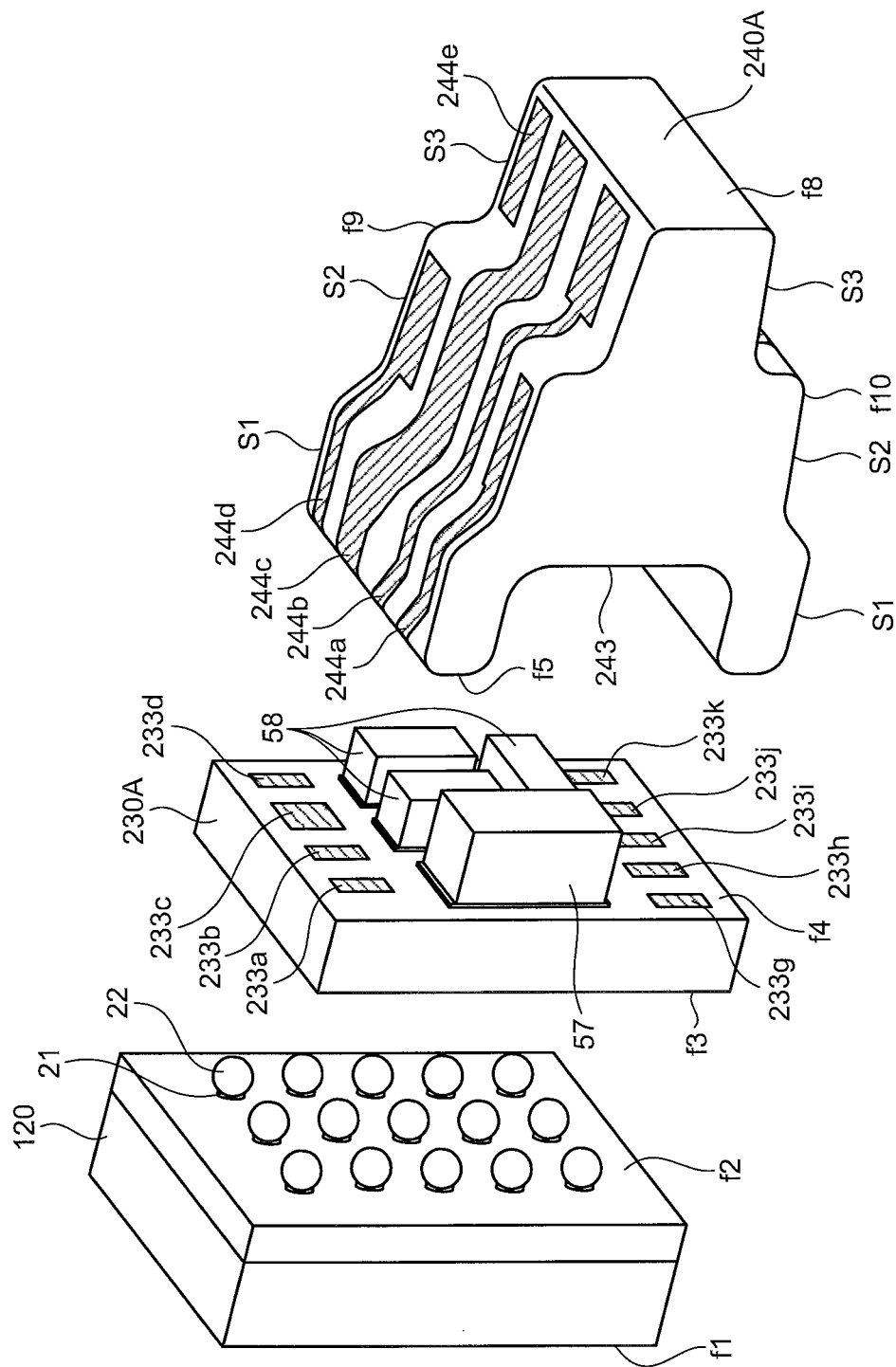

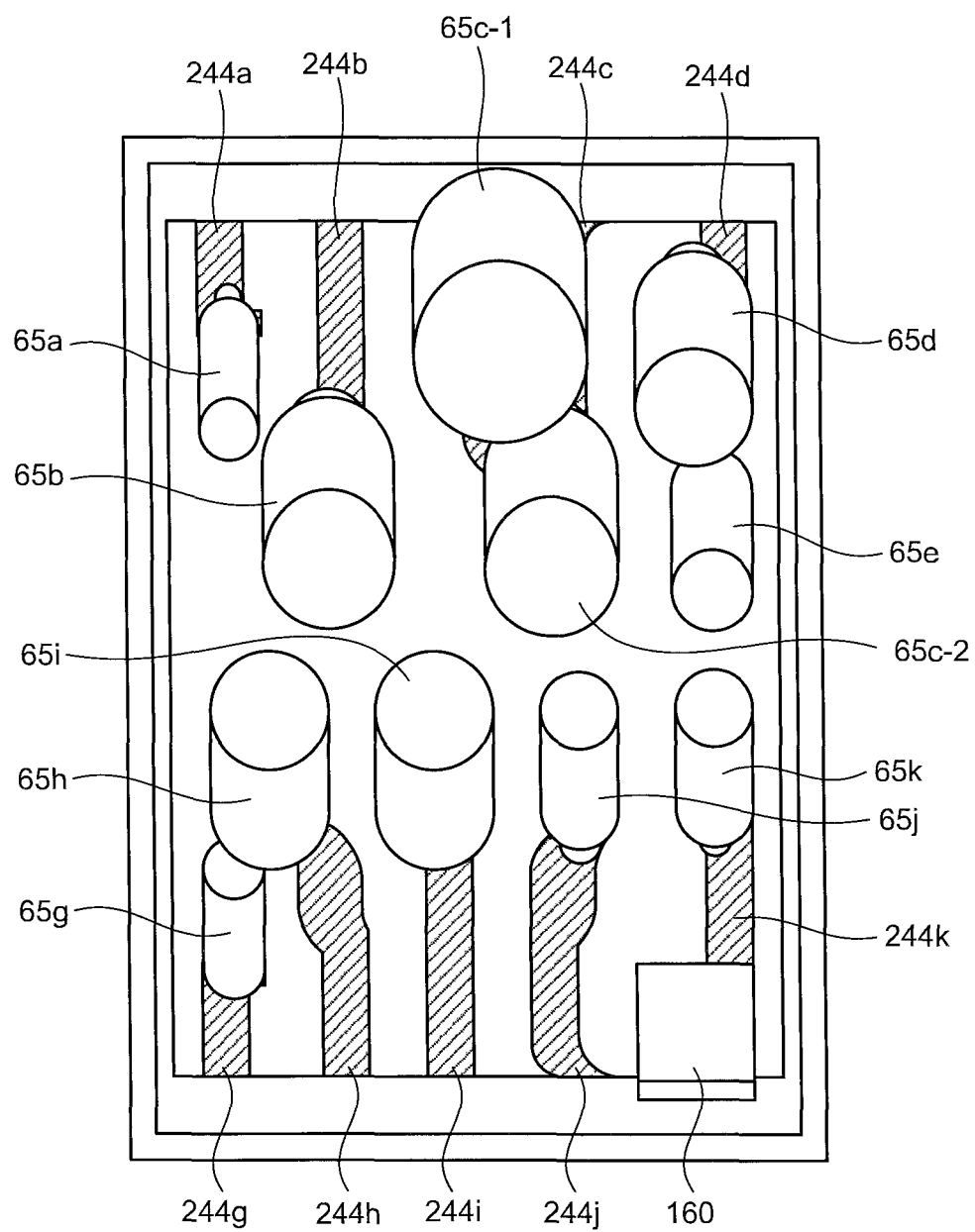

IMAGING UNIT, IMAGING MODULE, AND ENDOSCOPE SYSTEM HAVING A CIRCUIT BOARD WITH A RECESS

CROSS REFERENCES TO RELATED APPLICATIONS

This application is a continuation of PCT international application Ser. No. PCT/JP2015/080964, filed on Nov. 2, 2015 which designates the United States, incorporated herein by reference, and which claims the benefit of priority from Japanese Patent Application No. 2014-248300, filed on Dec. 8, 2014, incorporated herein by reference.

BACKGROUND

1. Technical Field

The disclosure relates to an imaging unit provided at a distal end of an insertion unit of an endoscope configured to be inserted into a subject to image an inside of the subject. The disclosure also relates to an imaging module and an endoscope system.

2. Related Art

In the related art, endoscope devices are widely used for various examinations in medical fields and industrial fields. Among them, in medical endoscope devices, a flexible insertion unit having an elongated shape where an image sensor is provided at a distal end thereof is inserted into a body cavity of a subject such as a patient, and thus, an in-vivo image in the body cavity can be acquired without making an incision. In addition, a treatment tool is allowed to protrude from the distal end of the insertion unit to perform therapeutic treatment if necessary. Therefore, the medical endoscope devices have been widely used.

An imaging unit including an image sensor and a circuit board where electronic components such as condensers or IC chips constituting a driving circuit for the image sensor are mounted is fitted into the distal end of the insertion unit of the endoscope device, and the circuit board of the imaging unit is connected to a cable by solder.

In recent years, for the purpose of simplifying an operation of connecting a signal line of the cable, improving reliability of connected portions, or miniaturizing, imaging units where a circuit board connected to an image sensor is formed in a steric structure have been proposed (for example, refer to JP 2005-278760 A; JP 2006-223624 A; JP 2000-199863 A; JP 2013-197501 A; and JP 2014-110847 A).

SUMMARY

In some embodiments, an imaging unit includes: a semiconductor package having an image sensor and having a connection electrode on a back side thereof; a circuit board having connection electrodes on front and back sides thereof, the connection electrode on the front side being connected to the connection electrode of the semiconductor package; a deformed circuit board having at least first, second, and third faces and having connection electrodes on the first, second, and third faces, respectively, a connection electrode of the connection electrodes on the first face being connected to the connection electrodes of the circuit board; an electronic component mounted on the back side of the circuit board; and a plurality of cables connected to the connection electrodes on the second and third faces of the deformed circuit board. The circuit board has a recess on the back side, or the deformed circuit board has a recess on the first face. The electronic component is housed in the recess of the circuit board or in the recess of the deformed circuit board. The circuit board, the deformed circuit board, and the plurality of cables connected to the connection electrodes on the second and third faces are located within a projection plane in an optical axis direction of the semiconductor package.

In some embodiments, an imaging module includes: a semiconductor package having an image sensor and having a connection electrode on a back side thereof; a circuit board having connection electrodes on front and back sides thereof, the connection electrode on the front side being connected to the connection electrode of the semiconductor package; a deformed circuit board having at least first, second, and third faces and having connection electrodes on the first, second, and third faces, respectively, a connection electrode of the connection electrodes on the first face being connected to the connection electrodes of the circuit board, a plurality of cables being connected to the connection electrodes on the second and third faces; and an electronic component mounted on the back side of the circuit board. The circuit board has a recess on the back side, or the deformed circuit board has a recess on the first face. The electronic component is housed in the recess of the circuit board or in the recess of the deformed circuit board. The circuit board and the deformed circuit board are located within a projection plane in an optical axis direction of the semiconductor package.

In some embodiments, an endoscope system includes an insertion unit in which the imaging unit is provided at a distal end of the insertion unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 20 is an exploded view of the imaging unit illustrated in FIG. 18; and

FIG. 21 is a schematic view of the imaging unit illustrated in FIG. 18 as viewed from the proximal end side.

DETAILED DESCRIPTION

Reference will be made below to endoscope systems including an imaging unit as modes for carrying out the present invention (hereinafter, referred to as "embodiment(s)"). The present invention is not limited to the embodiments. The same reference signs are used to designate the same elements throughout the drawings. The drawings are schematic ones, and thus, a relationship among thickness and widths of components, a ratio among the components, and the like are different from real ones. In addition, figures may include portions of which dimensions and ratios are different.

First Embodiment

Figure 1:
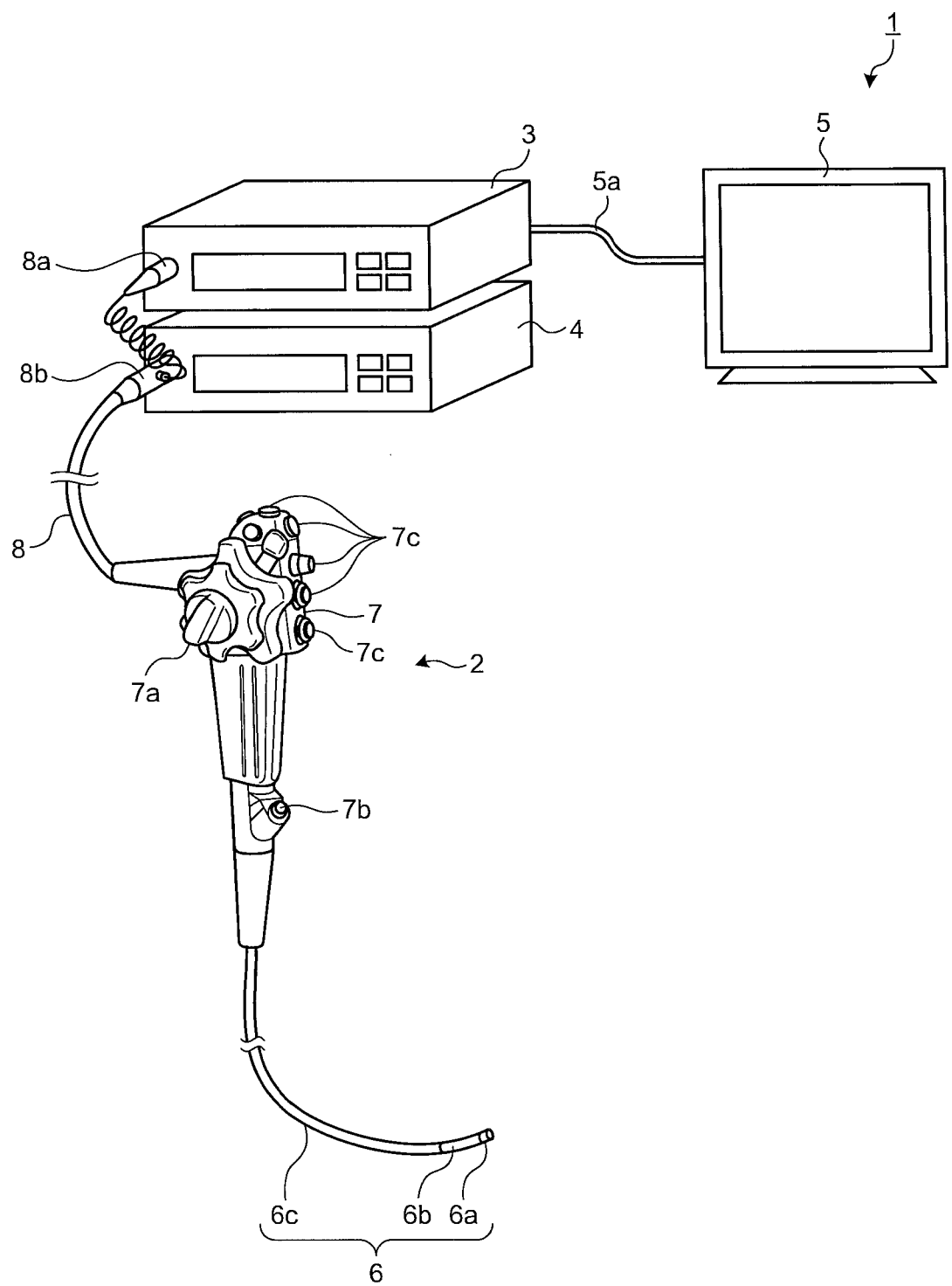
FIG. 1 is a schematic view illustrating an overall configuration of an endoscope system according to a first embodiment of the present invention.

FIG. 1 is a schematic view illustrating an overall configuration of an endoscope system according to a first embodiment of the present invention. As illustrated in FIG. 1, an endoscope system 1 according to the first embodiment is configured to include an endoscope 2 configured to be inserted into a subject and to image an inside of the subject to generate an in-vivo image signal of the subject, an information processing device 3 which performs a predetermined image process on the image signal obtained by the capturing of the endoscope 2 and controls components of the endoscope system 1, a light source device 4 which generates illumination light of the endoscope 2, and a display device 5 which displays an image of the image signal which is image-processed by the information processing device 3.

The endoscope 2 is configured to include an insertion unit 6 configured to be inserted into the subject, an operating unit 7 which is a proximal end side of the insertion unit 6 and is gripped by an operator, and a flexible universal cord 8 which extends from the operating unit 7.

The insertion unit 6 is implemented by using an illumination fiber (light guide cable), an electric cable, and an optical fiber, or the like. The insertion unit 6 includes a distal end portion 6a incorporating an imaging unit described later, a bendable bending portion 6b configured with a plurality of bending pieces, and a flexible tube portion 6c having flexibility and being provided to a proximal end side of the bending portion 6b. The distal end portion 6a is provided with an illumination unit which illuminates the inside of the subject through an illumination lens, an observation unit configured to image the inside of the subject, an opening which communicates with a treatment tool channel, and air/water supply nozzle (not illustrated).

The operating unit 7 includes a bending knob 7a bending the bending portion 6b in the up/down direction and the left/right direction, a treatment tool insertion unit 7b inserting a treatment tool such as biological forceps and laser scalpel into a body cavity of the subject, and a plurality of switches 7c performing operations of peripheral devices such as the information processing device 3, the light source device 4, an air supply device, a water supply device, and a gas supply device. The treatment tool inserted from the treatment tool insertion unit 7b is exposed to the opening in the distal end of the insertion unit 6 through the treatment tool channel provided inside the operating unit 7.

The universal cord 8 is configured by using an illumination fiber, a cable, or the like. The universal cord 8 is branched at the proximal end. The branched one end is a connector 8a, and the other proximal end is a connector 8b. The connector 8a is detachable to a connector of the information processing device 3. The connector 8b is detachable to the light source device 4. The universal cord 8 allows the illumination light emitted from the light source device 4 to propagate through the connector 8b and an illumination fiber to the distal end portion 6a In addition, the universal cord 8 transmits the image signal obtained by the capturing of the imaging unit described later through a cable and the connector 8a to the information processing device 3.

The information processing device 3 performs a predetermined image process on the image signal output from the connector 8a and controls the overall endoscope system 1.

The light source device 4 is configured by using a light source emitting light, a condenser lens, and the like. Under the control of the information processing device 3, the light source device 4 allows the light source to emit light and supplies the light as illumination light for the subject as an object to the endoscope 2 connected through the connector 8b and the illumination fiber of the universal cord 8.

The display device 5 is configured by using a display or the like using a liquid crystal display or an organic EL (Electro Luminescence) device. The display device 5 displays various types of information including images obtained from a predetermined image process performed by the information processing device 3 through an image cable 5a. The operator operates the endoscope 2 while viewing the image (in-vivo image) displayed on the display device 5, so that the operator can observe a desired position in the subject and determine properties and state of the position.

Figure 2:
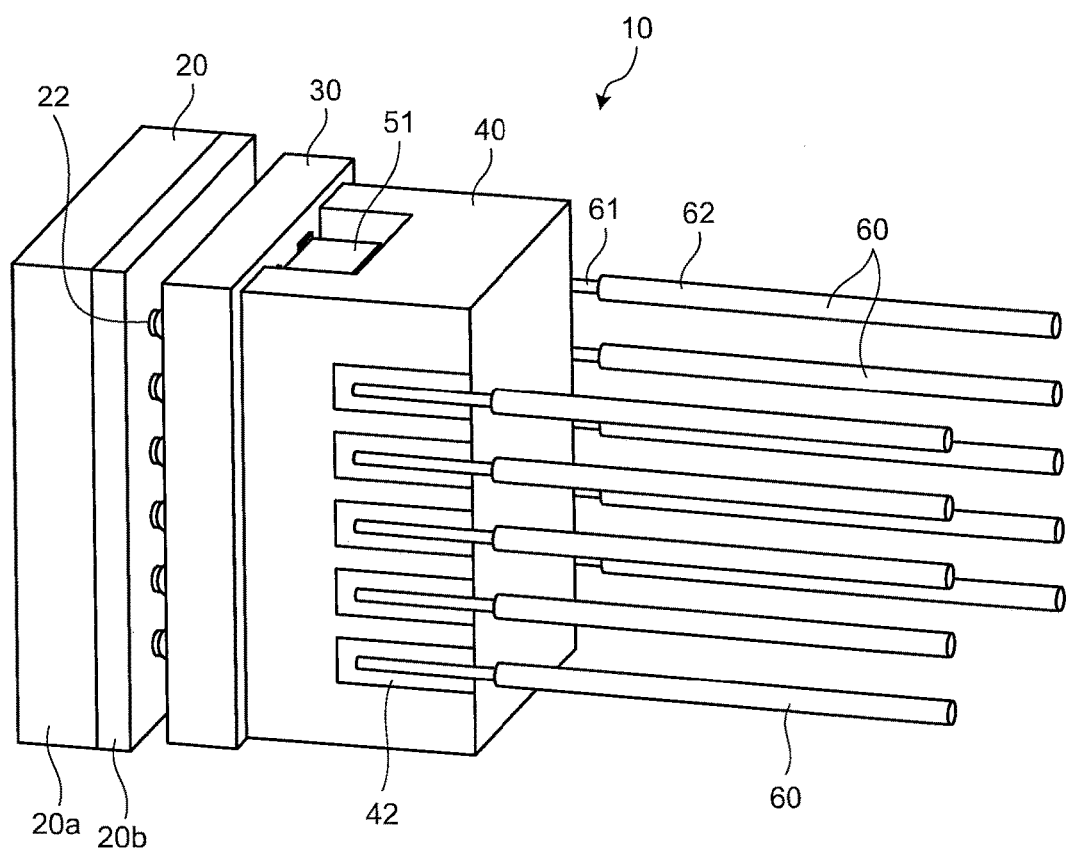
FIG. 2 is a perspective view of an imaging unit arranged in a distal end portion of an endoscope illustrated in FIG. 1.
Figure 3:
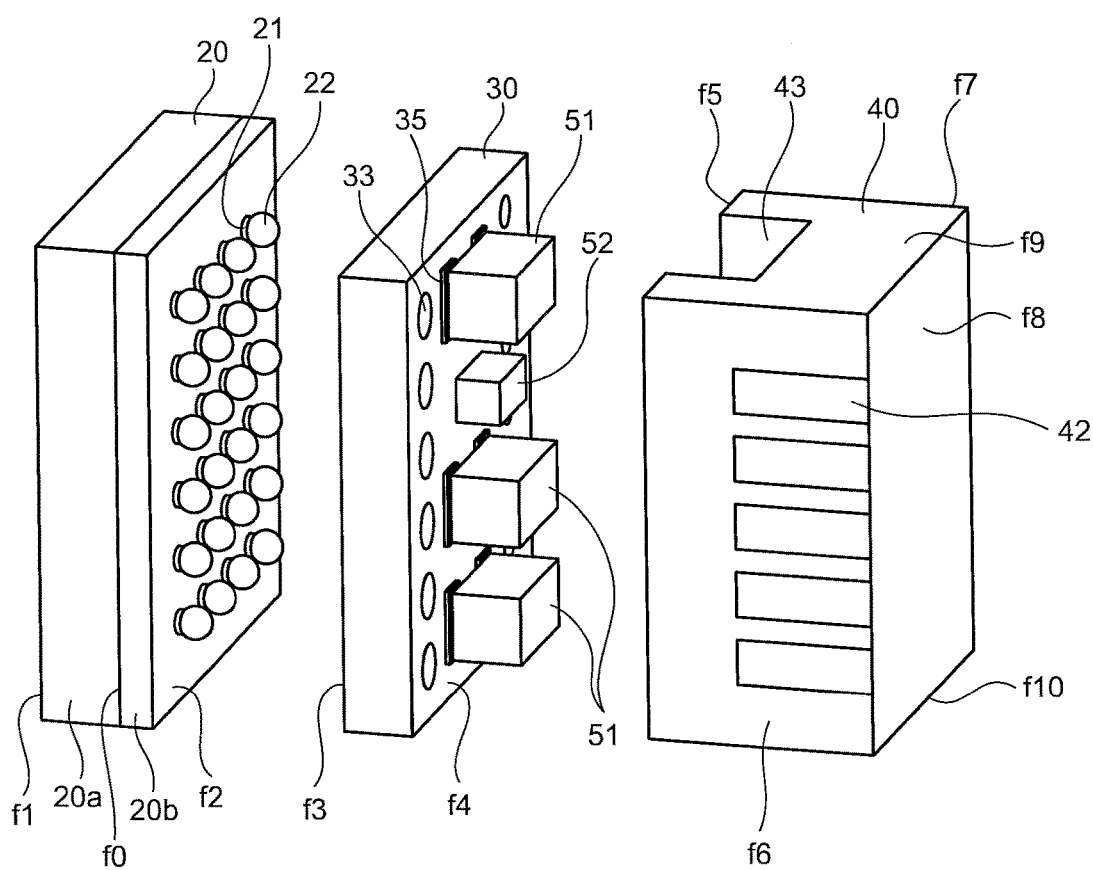
FIG. 3 is an exploded view of the imaging unit illustrated in FIG. 2.
Figure 4:
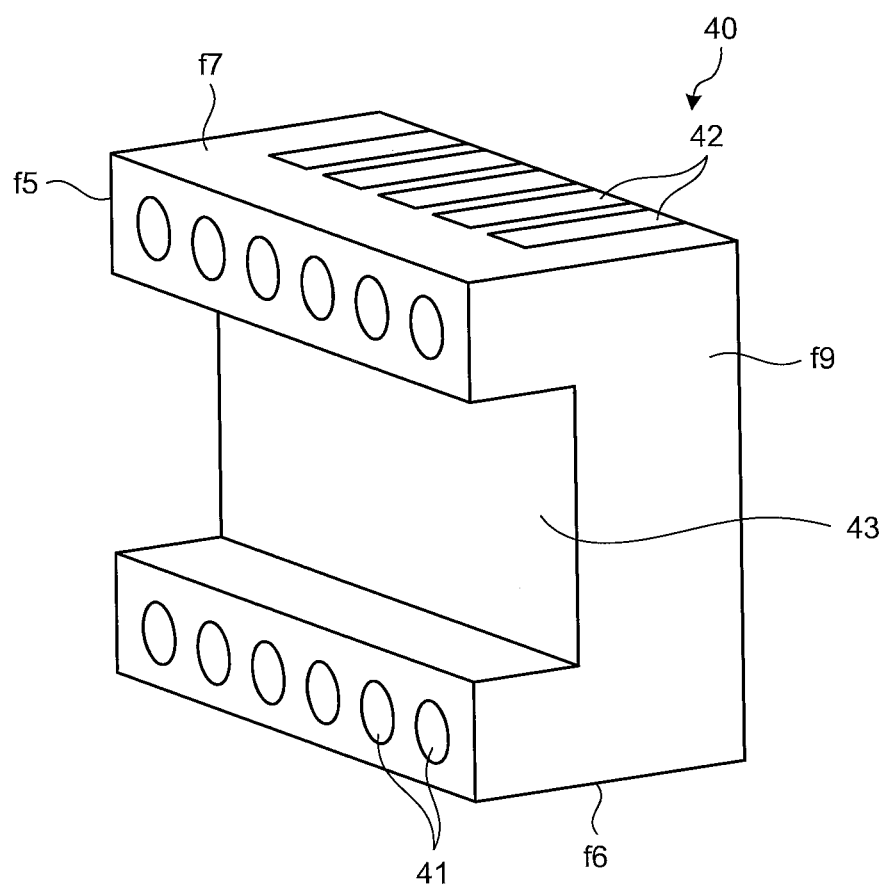
FIG. 4 is a perspective view of a bottom side of a deformed circuit board used in the imaging unit of FIG. 2.

Next, the imaging unit used in the endoscope system 1 will be described in detail. FIG. 2 is a perspective view of the imaging unit arranged in the distal end portion of the endoscope illustrated in FIG. 1. FIG. 3 is an exploded view of the imaging unit illustrated in FIG. 2. FIG. 4 is a perspective view of a bottom side of a deformed circuit board used in the imaging unit of FIG. 2.

An imaging unit 10 is configured to include a semiconductor package 20 which includes an image sensor and where connection electrodes 21 are formed on an f2 face that is a back side, a first circuit board 30 where connection electrodes are formed on an f3 face that is a front side and an f4 face that is a back side (the connection electrodes of the f3 face are not illustrated in the drawing and the connection electrodes of the f4 face are denoted by reference sign 33) and the connection electrodes of the f3 face are electrically and mechanically connected to the connection electrodes 21 of the semiconductor package 20, a deformed circuit board 40 where connection electrodes 41 and 42 are formed on an f5 face that is a first face and on f6 and f7 faces that are second and third faces, respectively, and the connection electrodes 41 of the f5 face that is the first face are electrically and mechanically connected to the connection electrodes 33 of the circuit board 30, electronic components 51 and 52 which are mounted on the f4 face that is the back side of the circuit board 30, and a plurality of cables 60 which are electrically and mechanically connected to the connection electrodes 42 of the f6 and f7 faces that are second and third faces of the deformed circuit board 40.

In the first embodiment, the electronic components 51 and 52 are housed in a recess 43 on the f5 face of the deformed circuit board 40. The circuit board 30, the deformed circuit board 40, and the cables 60 connected to the connection electrodes 42 of the f6 and f7 faces is located within a projection plane in an optical axis direction of the semiconductor package 20.

The semiconductor package 20 has a structure where glass 20*a* is adhered to an image sensor 20*b*. Light collected by a lens unit is incident on an f0 face (light-receiving plane) of the image sensor 20*b* including a light receiving portion through an f1 face that is the front side of the glass 20*a*. The connection electrodes 21 and bumps 22 made of solder or the like are formed on an f2 face (back side) of the image sensor 20*b*. Preferably, the semiconductor package 20 is a CSP (Chip Size Package) where wiring, electrode formation, resin sealing, and dicing are formed on an image sensor chip in a wafer state, and finally, a size of the image sensor chip becomes the size of the semiconductor package.

The circuit board 30 formed in a plate shape where a plurality of substrates where wire lines are formed are layered (a plurality of substrates parallel to the f3 face and the f4 face is layered). As the multi-layer substrate, used is a ceramic substrate, a glass epoxy substrate, a flexible substrate, a glass substrate, a silicon substrate, or the like. A plurality of vias 32 which conductively connects the wire lines on the multi-layer substrate is formed inside the circuit board 30 (refer to FIG. 7). Mounting lands 35 where the electronic components 51 and 52 are mounted are provided on the f4 face of the circuit board 30. The connection electrodes 33 of the f4 face and the mounting lands 35 are connected to the connection electrodes of the f3 face by the vias 32. As the electronic components 51 and 52, there may be exemplified passive parts such as capacitors, resistors, and coils and active parts such as driver ICs, waveform shaping circuit ICs, crystal oscillators, VCSELs, and PDs. In the first embodiment, as illustrated in FIG. 3, three electronic components 51 and one electronic component 52 are mounted. However, the types and numbers of mounted electronic components 51 and 52 are not limited thereto.

Connection electrodes (not illustrated) are formed on the f3 face of the circuit board 30 and are electrically and mechanically connected to the connection electrodes 21 of the semiconductor package 20 through bumps 22. Connecting portions between the connection electrodes of the f3 face and the connection electrodes 21 of the f2 face are sealed by a sealing resin 23 (refer to FIG. 7).

Figure 5:
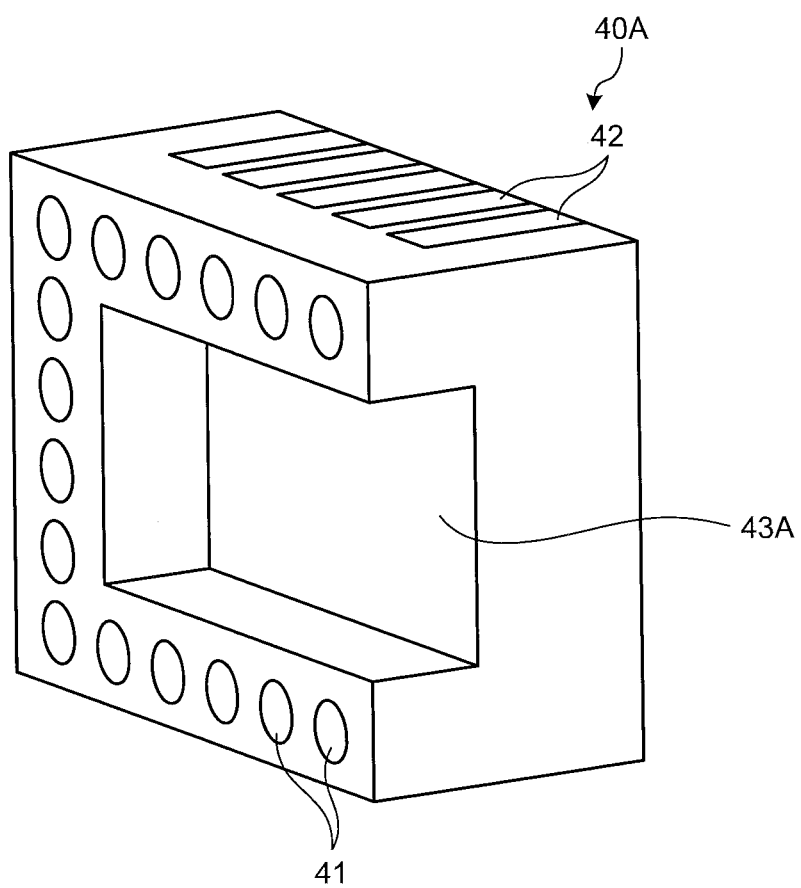
FIG. 5 is a perspective view of Modified Example 1 of the deformed circuit board.
Figure 6:
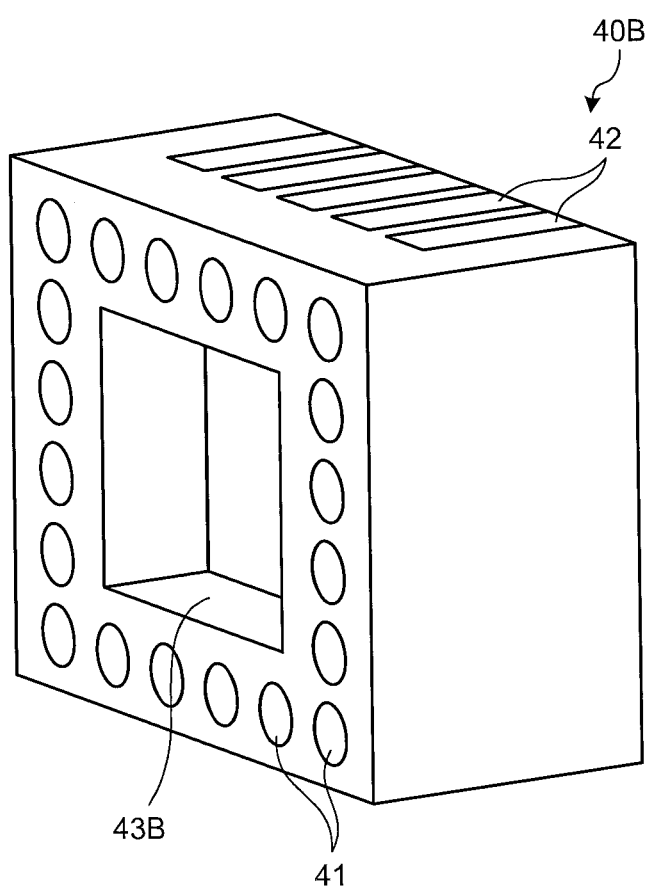
FIG. 6 is a perspective view of Modified Example 2 of the deformed circuit board.

The deformed circuit board 40 is made of a ceramic substrate, a glass epoxy substrate, a silicon substrate, or the like and forms an irregular shape by layering a plurality of substrates where wire lines are formed (a plurality of substrates parallel to the f5 face and the f8 face). As illustrated in FIG. 4, the recess 43 is formed on the f5 face of the deformed circuit board 40, and the recess 43 penetrates from an f9 face to an f10 face. The recess 43 has a size of accommodating the electronic components 51 and 52 mounted on the f4 face of the circuit board 30. In the first embodiment, the f2 face that is the back side of the semiconductor package 20 and the f3 face of the circuit board 30 are connected to each other, and the electronic components 51 and 52 are mounted in the vicinity of the center of the circuit board 30, so that the distance between the image sensor and the electronic components can be shortened. Therefore, impedance can be reduced, and the stable driving of the image sensor can be performed, so that high-quality image can be obtained. In addition, the recess 43 is provided on the f5 face of the deformed circuit board 40 to accommodate the electronic components 51 and 52, so that the length of a hard portion (optical-axis-direction length of a hard portion of the imaging unit 10) can be shorted. The recess 43 of the deformed circuit board 40 is not limited to the recess illustrated in FIG. 4. Examples of the recess include a recess 43A of a deformed circuit board 40A in which an opening is provided only on one face (f9 face) as illustrated in FIG. 5, or a recess 43B of a deformed circuit board 40B in which no opening is provided except for the f5 face as illustrated in FIG. 6. In the first embodiment, the recess 43 is opened in the f9 face and the f10 face. However, the recess may be opened in the f6 and f7 faces where the connection electrodes 42 are formed. The shape of the recess 43 may be appropriately selected according to shapes, mount positions, and the like of the electronic components 51 and 52.

Figure 7:
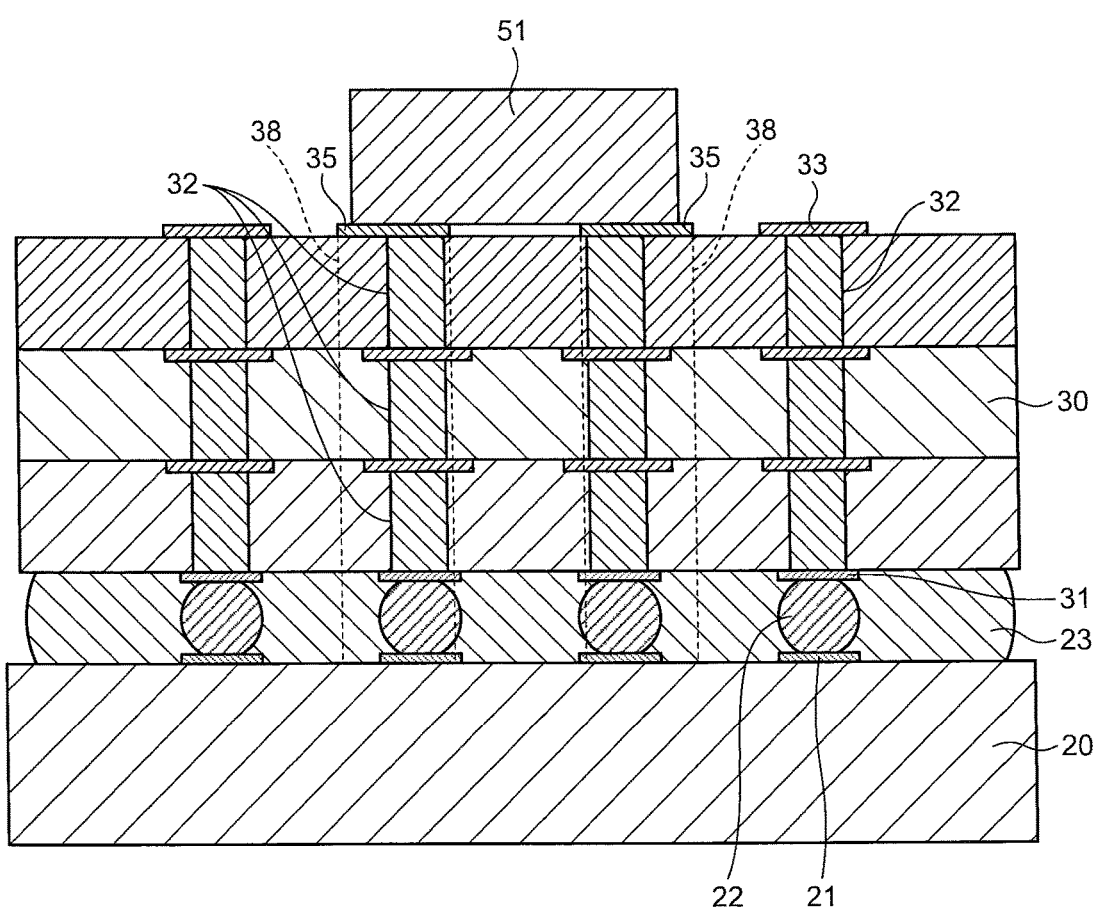
FIG. 7 is a partial cross-sectional view of the imaging unit illustrated in FIG. 3.
Figure 8:
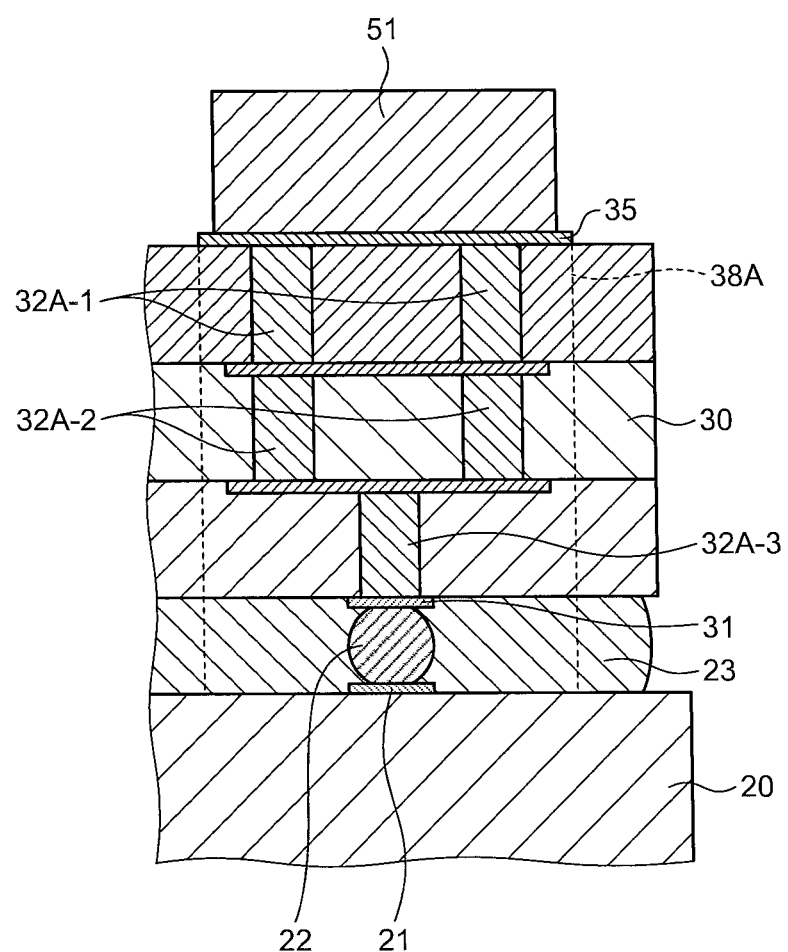
FIG. 8 is a cross-sectional view illustrating arrangement of electronic components and connection electrodes.

In the imaging unit 10, the vias 32 connecting at least a part of the connection electrodes 21 of the semiconductor package 20 and a connection electrodes 31 of the f3 face and the mounting lands 35 of the circuit board 30 are arranged within an optical-axis-direction projection plane of the mounting lands 35 of the electronic components 51 or 52. FIG. 7 is a partial cross-sectional view of the imaging unit illustrated in FIG. 3. As illustrated in FIG. 7, the connection electrodes 21 of the semiconductor package 20 are arranged within an optical-axis-direction projection area 38 of the mounting lands 35 of the electronic components 51. In addition, the vias 32 connecting the connection electrodes 31 of the f3 face and the mounting lands 35 of the circuit board 30 are arranged. In the first embodiment, since the electronic components 51 are connected to the image sensor in the semiconductor package 20 in a straightly-lined manner through the straight-line-shaped vias 32 and the connection electrodes 21, the impedance between the image sensor and the electronic components 51 can be decreased, so that noise can be reduced. In addition, the via 32 arranged in the projection area 38 may have a structure illustrated in FIG. 8. In FIG. 8, a plurality of vias 32A are arranged in an optical-axis-direction projection area 38A of the mounting lands 35 of the electronic components 51. Two vias 32A-1 and two vias 32A-2 are arranged in a first layer just below the mounting land 35 and a second layer as the subsequent layer, respectively, and one via 32A-3 is conductively connected in a final layer to be connected to the connection electrodes 31. In this case, the connection electrodes 21 of the semiconductor package 20 are arranged within the optical-axis-direction projection area 38A of the mounting lands 35 of the electronic components 51. In the structure of FIG. 8, since the plurality of vias 32A is arranged, in comparison with the case where one via is arranged, the impedance can be decreased, and the noise can be reduced.

The connection electrodes 41 are formed in the remaining portion except for the recess 43 of the f5 face of the deformed circuit board 40 and are connected to the connection electrodes 33 of the circuit board 30 by bonding using solder, Au—Au bonding using ultrasound, or the like. The connecting portions between the circuit board 30 and the deformed circuit board 40 and the recess 43 accommodating the electronic components 51 and 52 are sealed by a sealing resin (not illustrated).

The connection electrodes 42 connecting the cables 60 are provided on the f6 and f7 faces that are second and third faces of the deformed circuit board 40. An insulating outer coat 62 of one end portion of the cable 60 is peeled off, and an exposed conductor 61 is electrically and mechanically connected to the connection electrode 42 by solder (not illustrated). The f6 face that is the second face and the f7 face that is the third face are opposite to each other, and the connection electrodes 42 are provided to the opposite faces, so that the connection to the cables 60 is facilitated. In the first embodiment, although the connection electrodes 42 are formed on the f6 and f7 faces, the connection electrodes 42 may be formed on the f9 and f10 faces.

In the first embodiment, the board where the electronic components 51 and 52 and the cables 60 are mounted is divided into the circuit board 30 and the deformed circuit board 40, and the electronic components 51 and 52 are mounted in the vicinity of the center of the circuit board 30 close to the image sensor. Therefore, the impedance between the image sensor and the electronic components 51 and 52 can be decreased. In addition, with respect to terminals of the image sensor, there is a degree of freedom in that the terminals of the electronic components 51 and 52 are allowed to be close even to terminals in the vicinity of the center of the image sensor or to terminals in the outer periphery of the image sensor according to the situation. In addition, since the electronic components 51 and 52 are mounted on the back side of the circuit board and are accommodated in the recess 43 formed on the front side (f5 face) of the deformed circuit board 40, it is possible to change the arrangement configuration of the electronic components 51 and 52 more simply and inexpensively.

In addition, since the circuit board 30, the deformed circuit board 40, and cables 60 are located within the projection plane in the optical axis direction of the semiconductor package 20, it is possible to achieve a small diameter of the imaging unit 10. In addition, in the circuit board 30 and the deformed circuit board 40, the connection to the semiconductor package 20 or the connection between the circuit board 30 and the deformed circuit board 40 is performed on the f3, f4, and f5 faces where fine-pitch wire lines can be formed and which are parallel to the substrate surface, it is possible to obtain a small-sized, highly-reliable imaging unit 10.

Second Embodiment

Figure 9:
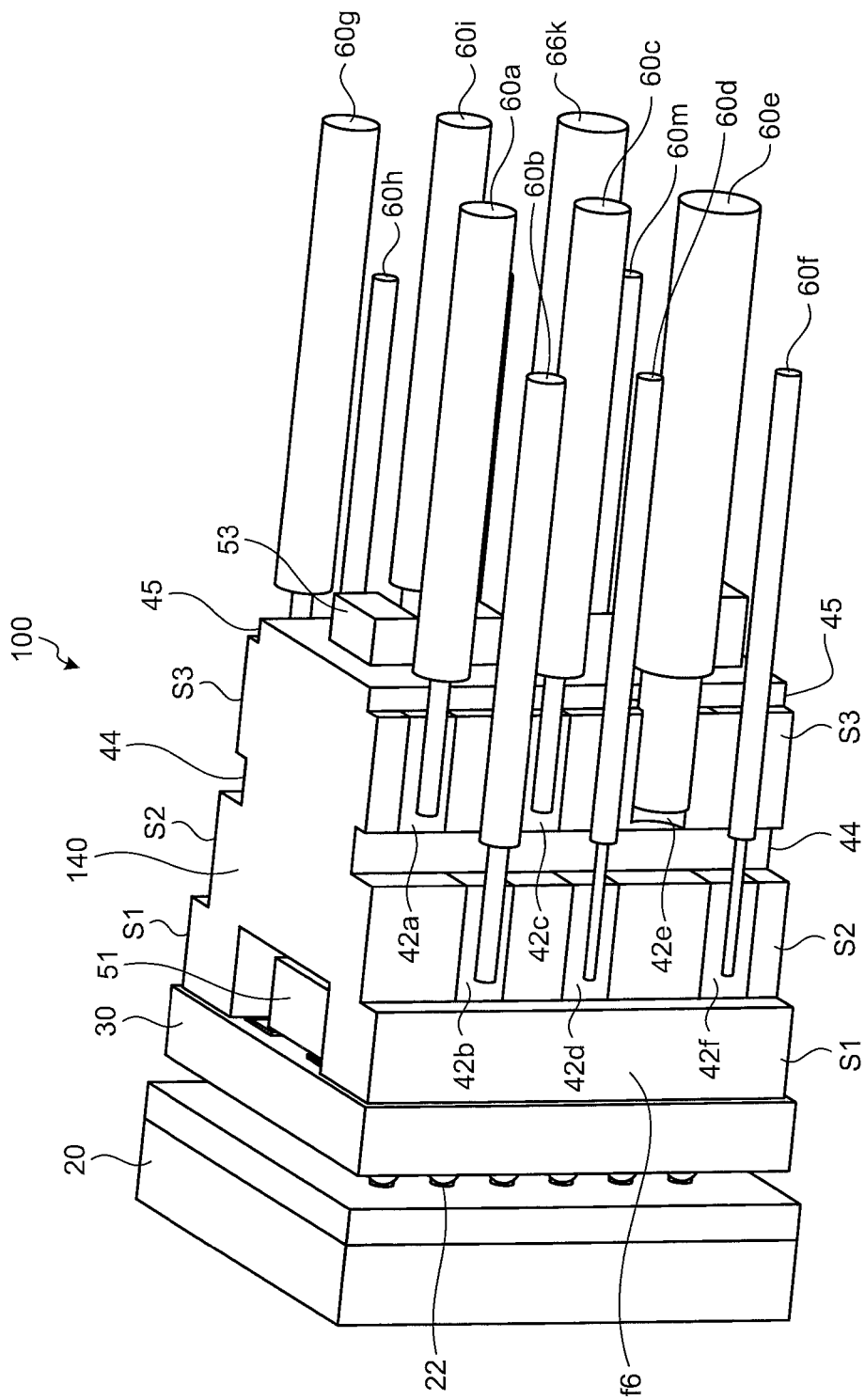
FIG. 9 is a perspective view of an imaging unit according to a second embodiment of the present invention.
Figure 10:
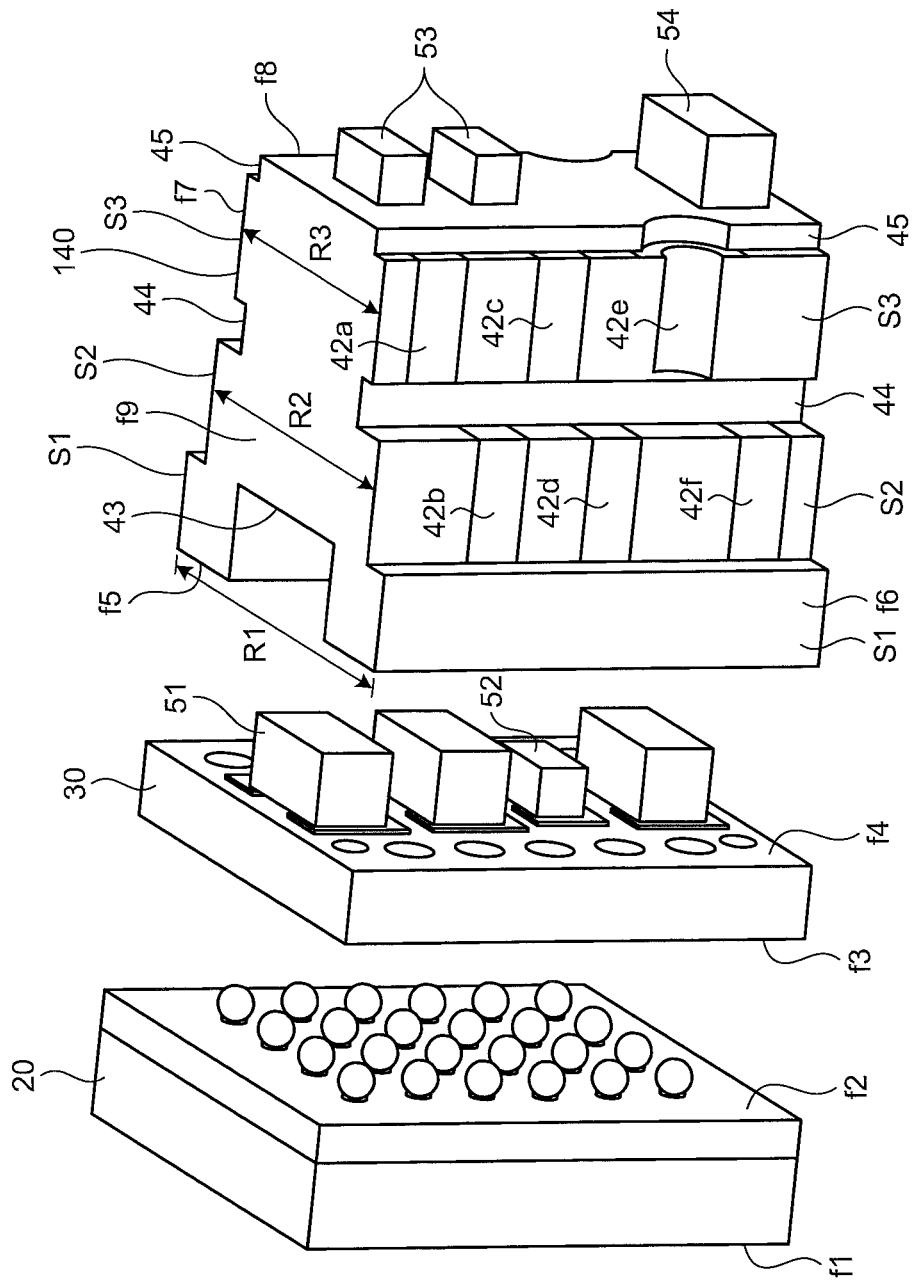
FIG. 10 is an exploded view of the imaging unit illustrated in FIG. 9.
Figure 11:
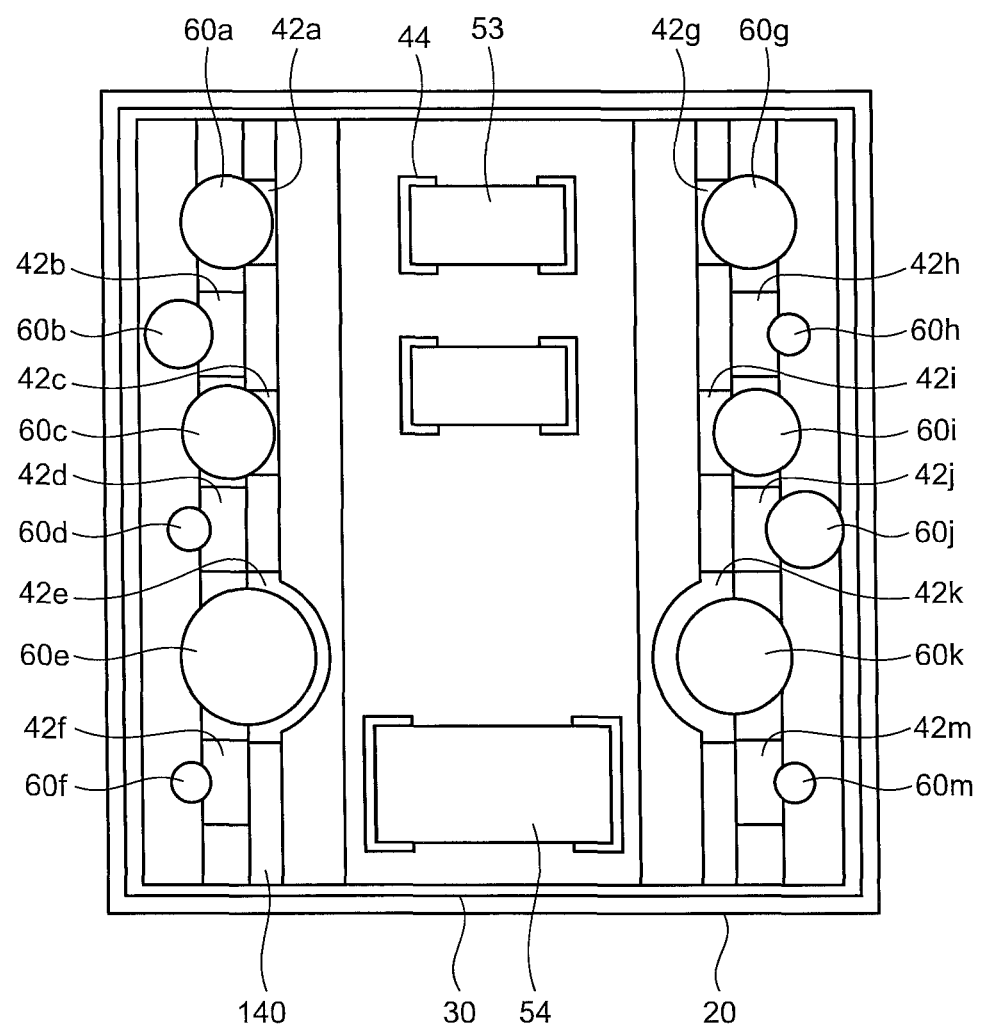
FIG. 11 is a schematic view of the imaging unit illustrated in FIG. 9 as viewed from the proximal end side.

In an imaging unit according to a second embodiment, second and third faces of a deformed circuit board are formed to have step shapes being close in an optical-axis-direction proximal end side of a semiconductor package. FIG. 9 is a perspective view of the imaging unit according to the second embodiment of the present invention. FIG. 10 is an exploded view of the imaging unit illustrated in FIG. 9. FIG. 11 is a schematic view of the imaging unit illustrated in FIG. 9 as viewed from the proximal end side.

In an imaging unit 100 according to the second embodiment, as illustrated in FIGS. 9 to 11, f6 and f7 faces that are second and third faces of a deformed circuit board 140 are formed to have step shapes being close in the optical-axis-direction proximal end side of the semiconductor package 20. That is, step portions S1, S2, and S3 are formed on the f6 and f7 faces.

In the step portions S2 and S3 of the f6 face, connection electrodes 42a, 42b, 42c, 42d, 42e, and 42f are formed, the connection electrodes 42a, 42b, 42c, 42d, 42e, and 42f are disposed in a staggered arrangement (zigzag shape). In addition, in the step portions S2 and S3 of the f7 face, connection electrodes 42g, 42h, 42i, 42j, 42k, and 42m are formed, and the connection electrodes 42g, 42h, 42i, 42j, 42k, and 42m are disposed in a staggered arrangement (zigzag shape). Cables 60a, 60b, 60c, 60d, 60e, and 60f are connected to the respective connection electrodes 42a, 42b, 42c, 42d, 42e, and 42f, and cables 60g, 60h, 60i, 60j, 60k, and 60m are connected to the respective connection electrodes 42g, 42h, 42i, 42j, 42k, and 42m.

The connection electrodes 42e and 42k have groove shapes where the deformed circuit board 140 is hollowed out. Conductors of the cables 60e and 60k are accommodated in the groove-shaped connection electrodes 42e and 42k. The connection electrodes 42e and 42k are formed to have the groove shapes and the conductors of the cables 60e and 60k are accommodated to be connected to the connection electrodes, and thus, even in the case where the cables 60e and 60k have large diameters, the cables can be located within the projection plane in the optical axis direction of the semiconductor package 20, so that it is possible to achieve a small diameter of the imaging unit 100. In addition, since the connection electrodes 42e and 42k are formed to have the groove shapes, the solder for cable connection is anchored in the multi-layer substrate constituting the deformed circuit board 140, and thus, the connection strength of the cables is improved, so that cable deviation does not easily occur even in the case of a cable having a large diameter.

The cables 60a to 60m have different outer diameters. Among the cables 60a to 60m, the cables 60e and 60k having the largest outer diameter are connected to the connection electrodes 42e and 42k provided in the step portion S3 that is the optical-axis-direction proximal end side. The f6 and f7 faces that are second and third faces are close in the optical-axis-direction proximal end side of the semiconductor package 20. That is, the width R2 of the step portion S2 on the proximal end side of the step portion S1 is smaller than the width R1 of the step portion S1, and the width R3 of the step portion S3 on the proximal end side of the step portion S2 is smaller than the width R2 of the step portion S2. Therefore, the cables 60e and 60k having the largest outer diameters are connected to the connection electrodes of the step portions S3 having the smallest diameters, and thus, the cables can be located within the projection plane in the optical axis direction of the semiconductor package 20, so that it is possible to achieve a small diameter of the imaging unit 100. In addition, the side surface of the step portions S1 and S2 have a function as positioning portions of the cables 60a to 60m which are to be connected to the step portions S2 and S3.

In addition, groove portions 44 are provided between the step portions S2 and S3, in other words, between the connection electrodes 42a, 42c, and 42e and the connection electrodes 42b, 42d, and 42f, and between the connection electrodes 42g, 42i, and 42k and the connection electrodes 42h, 42j, and 42m. In addition, groove portions 45 are provided in the optical-axis-direction proximal end sides of the connection electrodes 42a, 42c, and 42e and the connection electrodes 42g, 42i, and 42k. The groove portions 44 and 45 are provided, and thus, when the cables are connected to the connection electrodes, solder flow can be prevented, so that it is possible to reduce the risk of short circuit or the like. In addition, the groove portion 44 is coated with alumina, so that the solder flow can be further prevented.

In addition, mounting lands 47 are provided on the f8 face of the deformed circuit board 140, and electronic components 53 and 54 are mounted. Although it is preferable that electronic components are mounted on the circuit board 30, in the case where there are a large number of to-be-mounted electronic components, the electronic components may be mounted on the f8 face. For example, decoupling condensers or the like of which impedance is desired to be suppressed by being close to the image sensor may be mounted on the circuit board 30, and coupling condensers or the like of which impedance needs not to be suppressed by being close to the image sensor may be mounted on the f8 face.

In the second embodiment, since the second and third faces of the deformed circuit board 140 are formed to have stepped shapes being close in the optical-axis-direction proximal end side of the semiconductor package 20, even in the case where cables 60e and 60k or the like having large diameters are used, if the cables 60e and 60k are connected to the step portion S3 of the proximal end side, the cables 60e and 60k can be located within the projection plane in the optical axis direction of the semiconductor package 20, so that it is possible to achieve a small diameter of the imaging unit 100.

Figure 12:
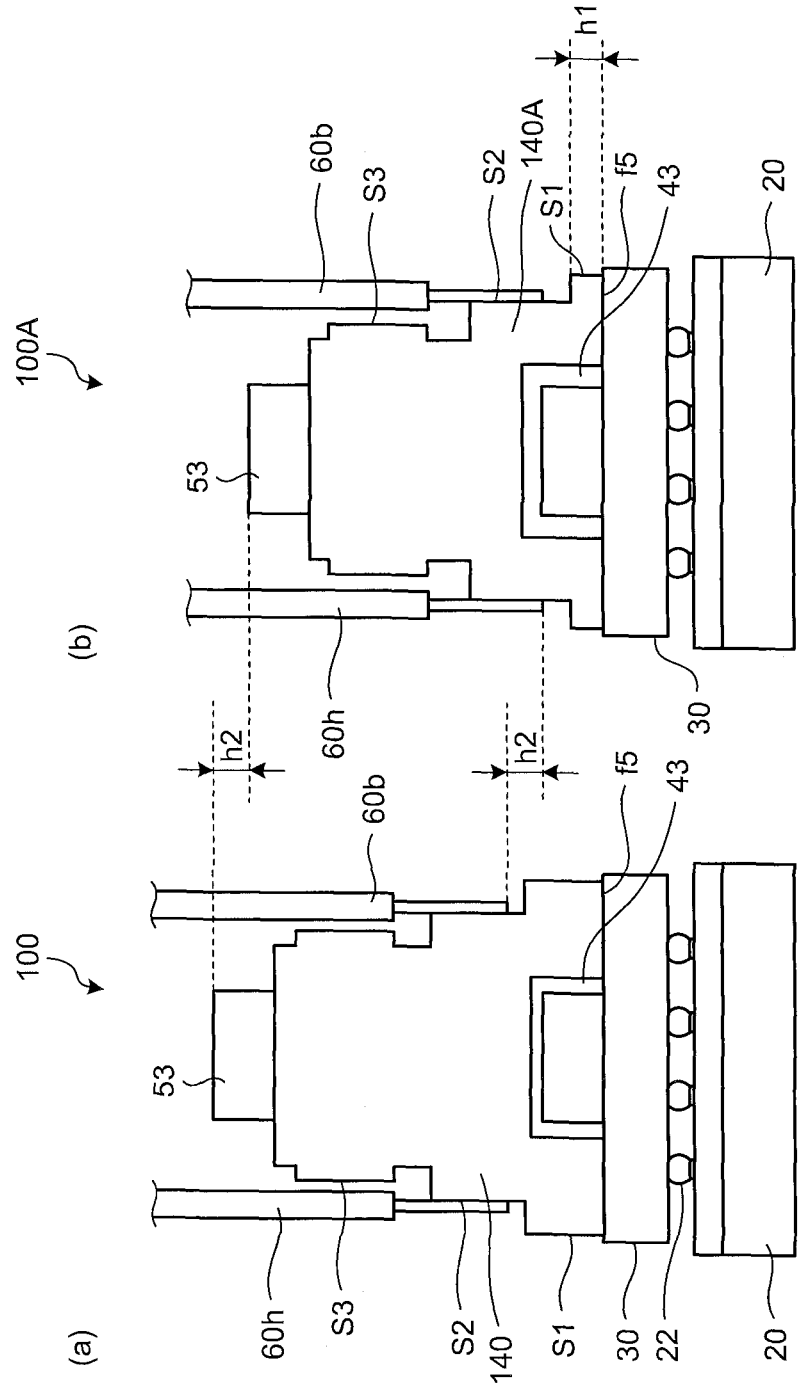
FIG. 12 is a side view of an imaging unit according to Modified Example of the second embodiment of the present invention.

In addition, in the second embodiment, although the connection electrodes 42b, 42d, and 42f, and connection electrodes 42h, 42j, and 42m arranged in the step portion S2 are formed in the proximal end side from the bottom face of the recess 43, the connection electrodes 42b, 42d, 42f, 42h, 42j, and 42m may be formed at the positions overlapping with the recess 43 in the optical axis direction. FIG. 12 is a side view of an imaging unit according to Modified Example of the second embodiment of the present invention. In FIG. 12, only the cables 60a and 60g are illustrated.

As illustrated in (b) of FIG. 12, in an imaging unit 100A according to Modified Example, a length h1 in the optical axis direction of the step portion S1 of a deformed circuit board 140A is small, and thus, a part of connection electrodes 42b, 42d, 42f, 42h, 42j, and 42m arranged on the step portion S2 is formed at the position overlapping with the recess 43 in the optical axis direction. Therefore, in Modified Example, the arrangement positions of the connection electrodes 42b, 42d, 42f, 42h, 42j, and 42m can be shifted by h2 toward the f5 face direction in comparison with the second embodiment illustrated in (a) of FIG. 12, so that the length of a hard portion of the imaging unit 100A can be shortened by h2.

Third Embodiment

Figure 13:
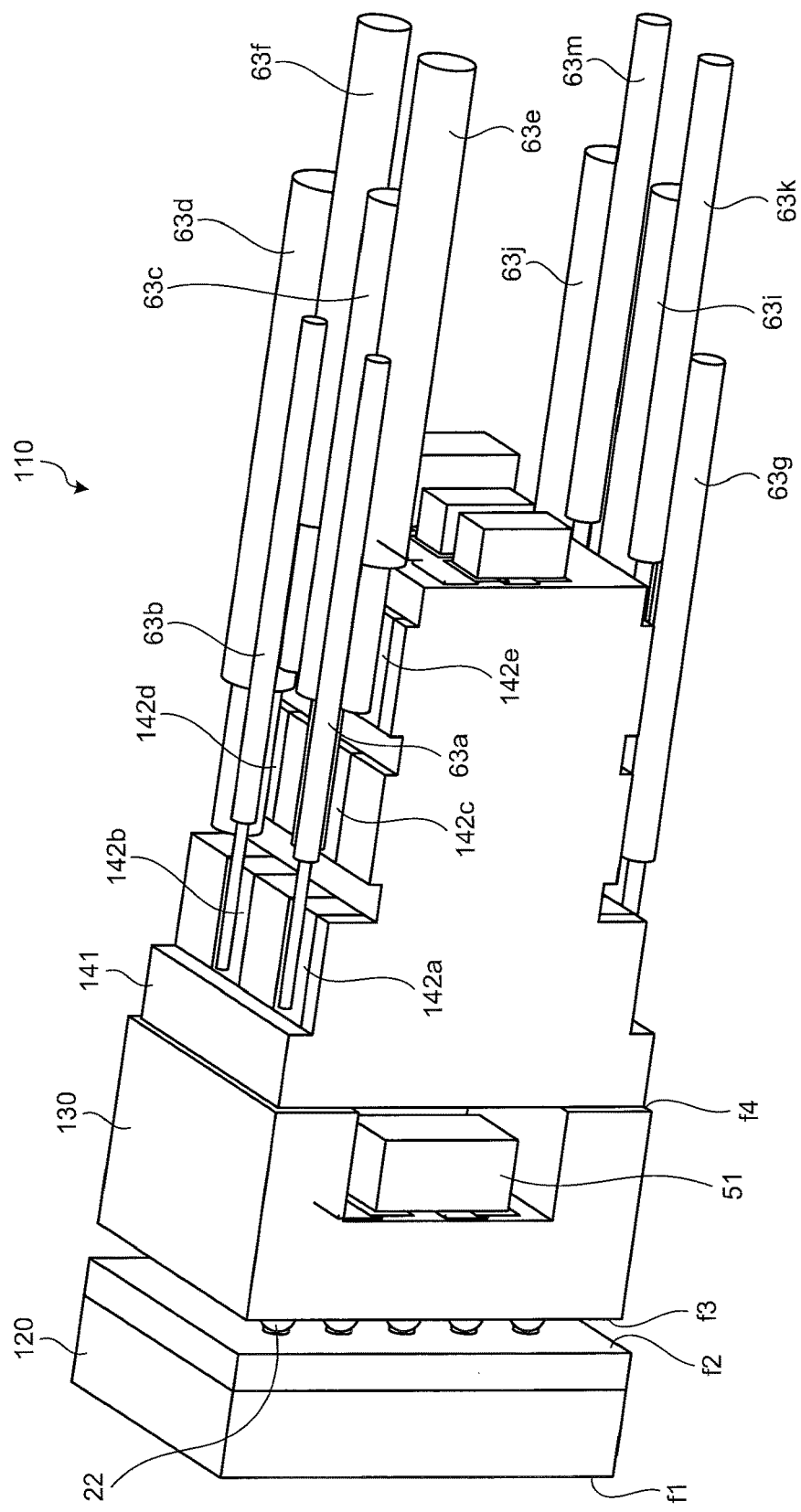
FIG. 13 is a perspective view of an imaging unit according to a third embodiment of the present invention.
Figure 14:
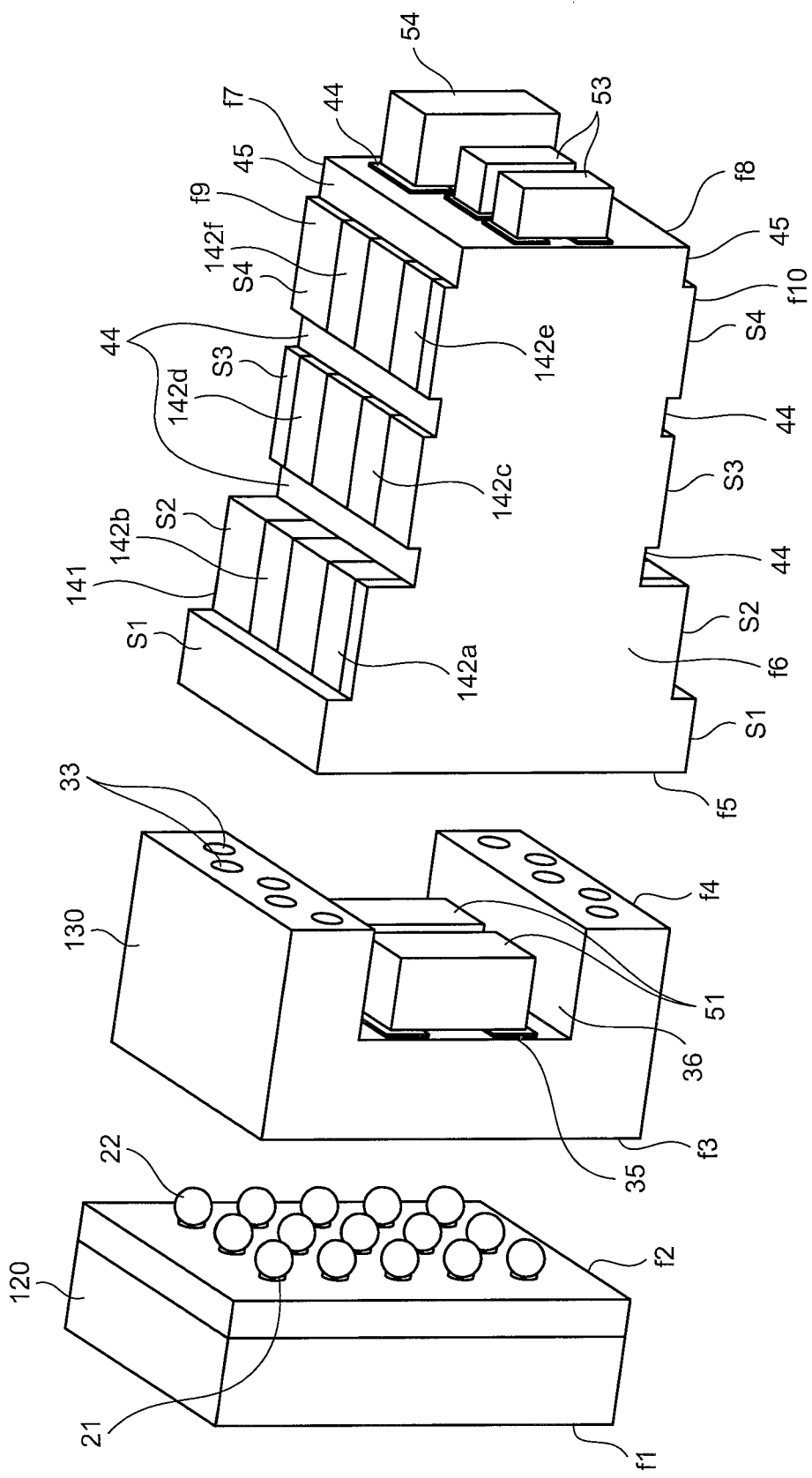
FIG. 14 is an exploded view of the imaging unit illustrated in FIG. 13.

In an imaging unit according to a third embodiment, electronic components are mounted in a recess formed in a circuit board. FIG. 13 is a perspective view of the imaging unit according to the third embodiment of the present invention. FIG. 14 is an exploded view of the imaging unit illustrated in FIG. 13.

In an imaging unit 110 according to the third embodiment, as illustrated in FIG. 13 and FIG. 14, a recess 36 is provided in an f4 face that is the back side of a circuit board 130. Electronic components 51 are mounted on mounting lands 35 in the recess 36.

In a semiconductor package 120, connection electrodes 21 and bumps 22 made of solder or the like are arranged on an f2 face that is the back side are connected to connection electrodes (not illustrated) formed on an f3 face that is the front side of the circuit board 130. Connection electrodes 33 are provided on an f4 face excluding the recess 36 of the circuit board 130 and are connected to connection electrodes (not illustrated) formed on an f5 face of a deformed circuit board 141.

In the deformed circuit board 141, step portions S1, S2, S3, and S4 are provided on f9 and f10 faces. In the third embodiment, the f9 face is a second face, and the f10 face is a third face. The step portions S1 to S4 are provided so that the f9 and f10 faces are close to each other in the optical-axis-direction proximal end side of the semiconductor package 120.

Connection electrodes 142a and 142b are arranged in the step portion S2 of the f9 face, connection electrodes 142c and 142d are arranged in the step portion S3, and connection electrodes 142e and 142f are arranged in the step portion S4. Connection electrodes 142g and 142h (not illustrated) are arranged in the step portion S2 of the f10 face, connection electrodes 142i and 142j (not illustrated) are arranged in the step portion S3, and connection electrodes 142k and 142m (not illustrated) are arranged in the step portion S4.

In addition, cables 63a, 63b, 63c, 63d, 63e, and 63f are connected to the connection electrodes 142a, 142b, 142c, 142d, 142e, and 142f, respectively. Cables 63g, 63h, 63i, 63j, 63k, and 63m are connected to the connection electrodes 142g, 142h, 142i, 142j, 142k, and 142m, respectively.

Groove portions 44 are provided between the step portions S2 and S3 and between the step portions S3 and S4, in other words, between the connection electrodes 142a and 142b and the connection electrodes 142c and 142d, between the connection electrodes 142c and 142d and the connection electrodes 142e and 142f, between the connection electrodes 142g and 142h and the connection electrodes 142i and 142j, and between the connection electrodes 142i and 142j and the connection electrodes 142k and 142m. In addition, groove portions 45 are provided in the optical-axis-direction proximal end sides of the connection electrodes 142e and 142f and in the optical-axis-direction proximal end side of the connection electrodes 142k and 142m. The groove portions 44 and 45 are provided, and thus, when the cables are connected to the connection electrodes, solder flow can be prevented, so that it is possible to reduce the risk of short circuit or the like.

In the third embodiment, the recess 36 is formed on the back side (f4 face) of the circuit board 130, and the electronic components 51 and the like are mounted in the recess 36. In the third embodiment, since the electronic components 51 and the like are mounted in the vicinity of the center of the circuit board 130 close to the image sensor, it is possible to decrease the impedance between the image sensor and the electronic components 51 and the like. In addition, since the electronic components 51 and the like are mounted in the recess 36 of the circuit board 130, it is possible to change the arrangement configuration of the electronic components 51 and the like more simply and inexpensively. Furthermore, if a recess is formed in the deformed circuit board 141, the board becomes expensive. However, in the third embodiment, since there is no need to form a recess in the deformed circuit board 141, it is possible to provide an inexpensive imaging unit. Furthermore, in the case where the recess 36 is formed in the circuit board 130, the stress exerted on the semiconductor package 20 can be reduced, so that it is possible to provide a highly-reliable imaging unit.

Fourth Embodiment

Figure 15:
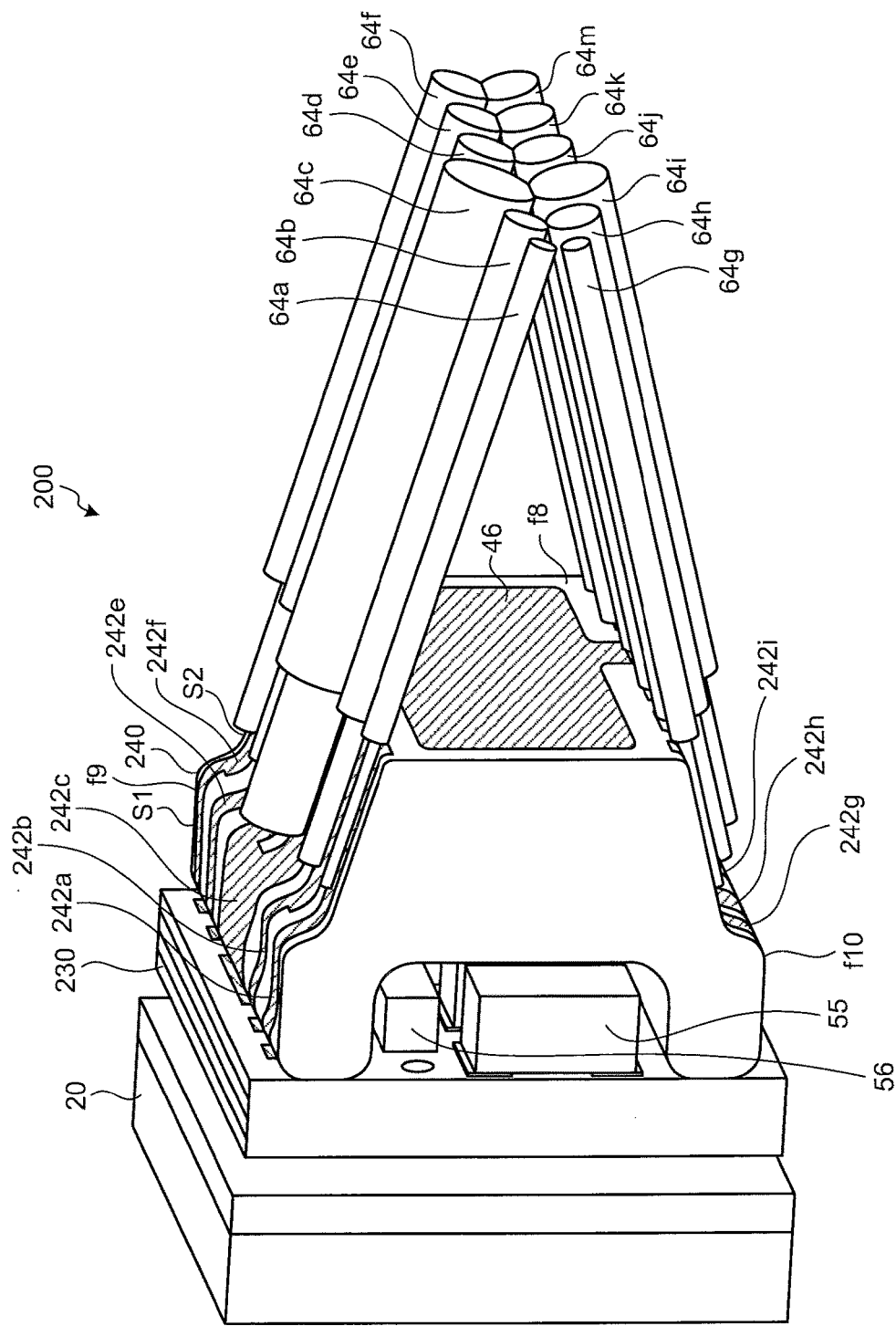
FIG. 15 is a perspective view of an imaging unit according to a fourth embodiment of the present invention.
Figure 16:
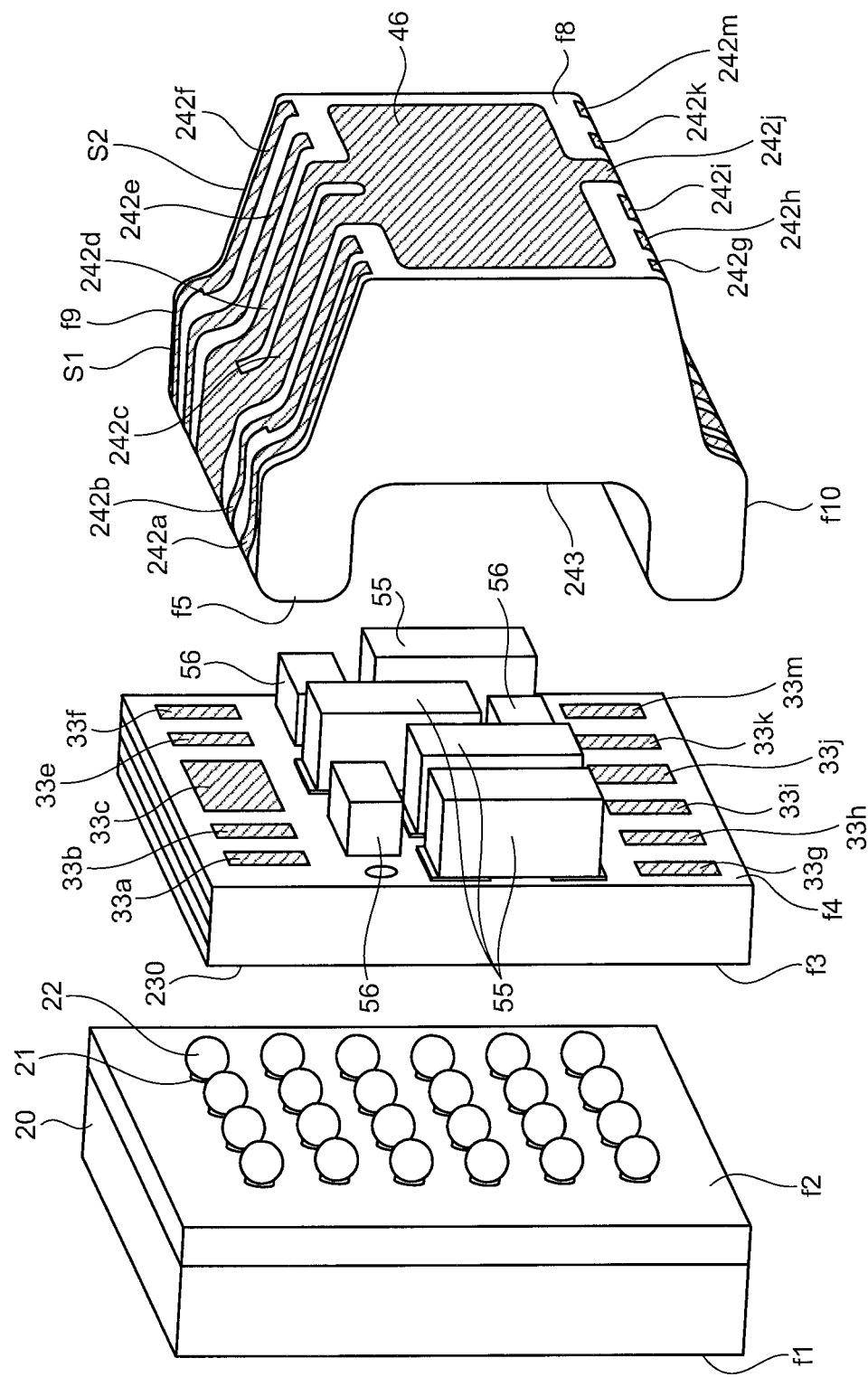
FIG. 16 is an exploded view of the imaging unit illustrated in FIG. 15.
Figure 17:
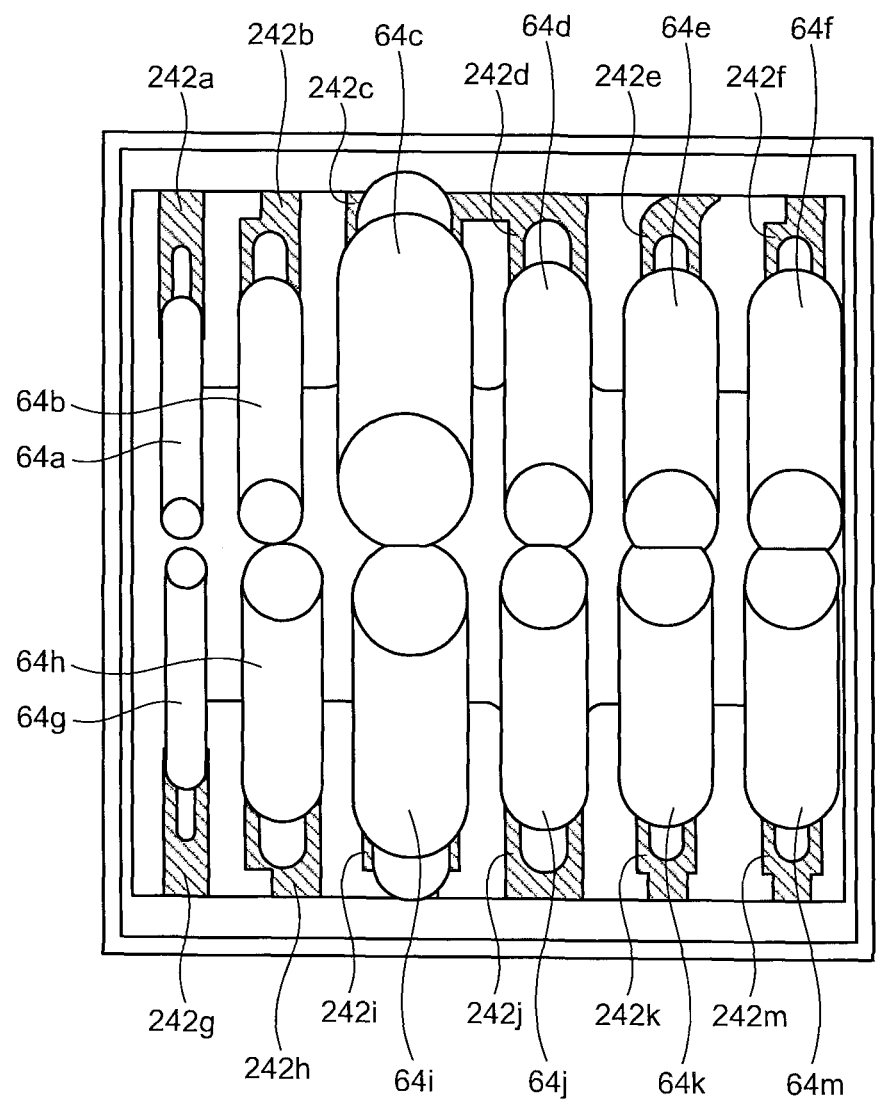
FIG. 17 is a schematic view of the imaging unit illustrated in FIG. 15 as viewed from the proximal end side.

In an imaging unit according to a fourth embodiment, each of second and third faces of a deformed circuit board has a gradient which is close in an optical-axis-direction proximal end side of a semiconductor package. FIG. 15 is a perspective view of the imaging unit according to the fourth embodiment of the present invention. FIG. 16 is an exploded view of the imaging unit illustrated in FIG. 15. FIG. 17 is a schematic view of the imaging unit illustrated in FIG. 15 as viewed from the proximal end side.

In an imaging unit 200 according to the fourth embodiment, as illustrated in FIGS. 15 to 17, f9 and f10 faces that are second and third faces of a deformed circuit board 240 have gradients which are close in the optical-axis-direction proximal end side of the semiconductor package 20. In the fourth embodiment, the deformed circuit board 240 is an MID (Molded Interconnect Device) board where steric wiring is formed by injection molding. In the fourth embodiment, since the MID board is used as the deformed circuit board 240, it is possible to manufacture the imaging unit more simply and inexpensively. As a base material of the MID board, there may be exemplified a liquid crystal polymer, a polyamide, a polycarbonate, or the like.

On an f4 face that is a back side of a circuit board 230, connection electrodes 33*a*, 33*b*, 33*c*, 33*e*, 33*f*, 33*g*, 33*h*, 33*i*, 33*j*, 33*k*, and 33*m* are provided, and mounting lands where electronic components 55 and 56 are mounted are provided.

On an f5 face of the deformed circuit board 240, a recess 243 is formed, and connection electrodes 241*a*, 241*b*, 241*c*, 241*e*, 241*f*, 241*g*, 241*h*, 241*i*, 241*j*, 241*k*, and 241*m* (not illustrated) are formed to be connected to the respective connection electrodes 33*a*, 33*b*, 33*c*, 33*e*, 33*f*, 33*g*, 33*h*, 33*i*, 33*j*, 33*k*, and 33*m* of the circuit board 230.

The f9 and f10 faces of the deformed circuit board 240 have gradients which are close in the optical-axis-direction proximal end side of the semiconductor package 20, preferably, gradients which form an isosceles triangle when the f9 and f10 faces extend. In addition, level difference portions S1 and S2 are provided to the f9 and f10 faces, and connection electrodes 242*a*, 242*b*, 242*c*, 242*d*, 242*e*, 242*f*, 242*g*, 242*h*, 242*i*, 242*j*, 242*k*, and 242*m* are arranged on the entire f9 and f10 faces. In addition, a ground pattern 46 which is connected to the connection electrodes 242*c*, 242*d*, and 242*j* is formed on the f8 face.

The connection electrodes 242*a*, 242*b*, 242*e*, 242*f*, 242*g*, 242*h*, 242*i*, 242*j*, 242*k*, and 242*m* extend from the connection electrodes 241*a*, 241*b*, 241*e*, 241*f*, 241*g*, 241*h*, 241*i*, 241*j*, 241*k*, and 241*m* of the f5 face to the f9 or f10 face, and the connection electrodes 242*c* and 242*d* are branched from the connection electrode 241*c* in the level difference portion S2 of the f9 face.

Cables 64*a*, 64*b*, 64*c*, 64*d*, 64*e*, 64*f*, 64*g*, 64*h*, 64*i*, 64*j*, 64*k*, and 64*m* are connected to the respective connection electrodes 242*a*, 242*b*, 242*c*, 242*d*, 242*e*, 242*f*, 242*g*, 242*h*, 242*i*, 242*j*, 242*k*, and 242*m* in the level difference portion S2.

The cables 64*a* to 64*m* are cables constituting a composite cable which bundles a plurality of cables and is covered with an outer coat shield and an outer coat. When the cables are to be connected to the connection electrodes, the outer coat shield and the outer coat of one end portion of the composite cable are peeled off, and after that, the individual cables 64*a* to 64*m* are decomposed to be connected. In the fourth embodiment, since the f9 and f10 faces have the gradients which are close in the optical-axis-direction proximal end side, in comparison with the case where the faces are horizontal, it is possible to easily perform the connection to the connection electrodes 242*a* to 242*m* of the cables 64*a* to 64*m* (to easily performing setting to a tool for connection to the cables 64*a* to 64*m*). In addition, since the cables 64*a* to 64*m* are arranged so as to extend along the f9 and f10 faces, the exposed portions from the outer coat shield of the cables 64*a* to 64*m* are shortened, so that external influence can be reduced.

In addition, since the connection electrodes 241*a*, 241*b*, 241*c*, 241*e*, 241*f*, 241*g*, 241*h*, 241*i*, 241*j*, 241*k*, and 241*m* of the f5 face (not illustrated) are formed up to the end point of the f5 face to become the connection electrodes 242*a*, 242*b*, 242*c*, 242*d*, 242*e*, 242*f*, 242*g*, 242*h*, 242*i*, 242*j*, 242*k*, and 242*m* of the f9 or f10 face, when the connection electrodes are to be connected to the respective connection electrodes 33*a*, 33*b*, 33*c*, 33*e*, 33*f*, 33*g*, 33*h*, 33*i*, 33*j*, 33*k*, and 33*m*, solder fillets are formed, so that it is possible to improve connection strength between the circuit board 230 and the deformed circuit board 240.

Figure 18:
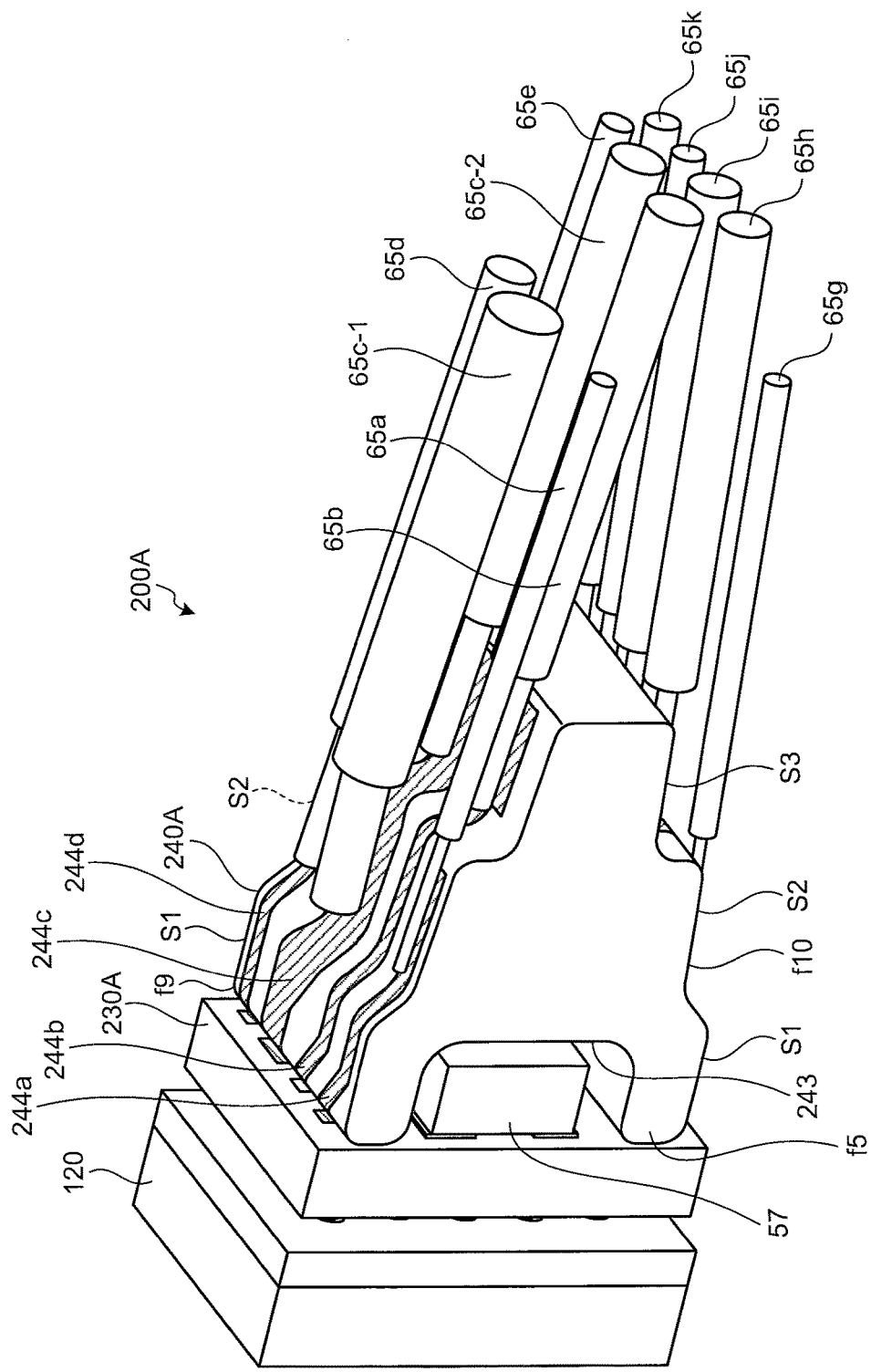
FIG. 18 is a perspective view of an imaging unit according to Modified Example of the fourth embodiment of the present invention.
Figure 19:
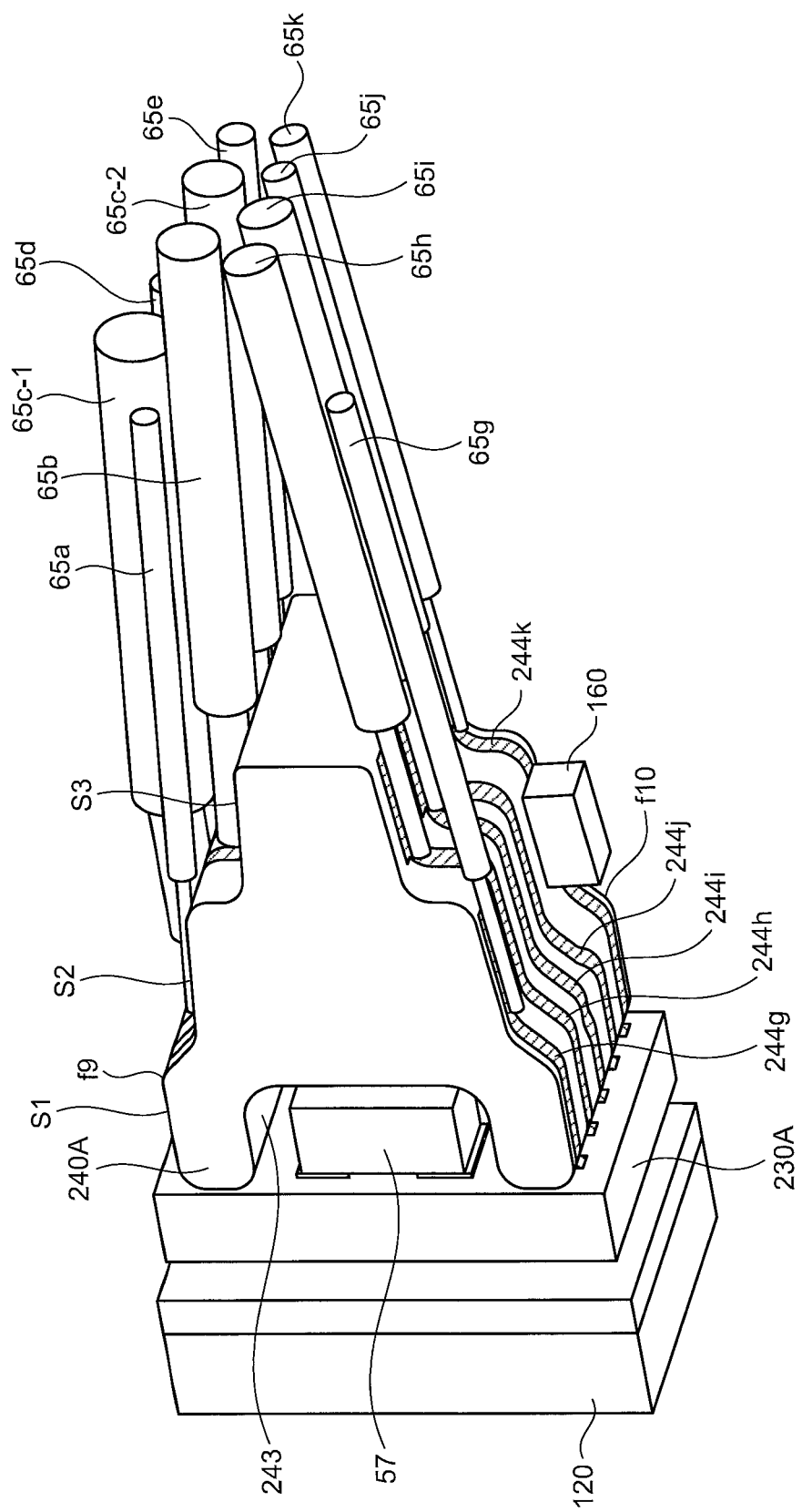
FIG. 19 is a perspective view of the imaging unit illustrated in FIG. 18 as viewed from the lower side.

Besides the cables, electronic components may be mounted on the second or third face of the deformed circuit board. FIG. 18 is a perspective view of an imaging unit according to Modified Example of the fourth embodiment of the present invention. FIG. 19 is a perspective view of the imaging unit illustrated in FIG. 18 as viewed from the lower side. FIG. 20 is an exploded view of the imaging unit illustrated in FIG. 18. FIG. 21 is a schematic view of the imaging unit illustrated in FIG. 18 as viewed from the proximal end side.

In an imaging unit 200A according to Modified Example of the fourth embodiment, an electronic component 160 is mounted on an f10 that is a third face.

On an f4 face that is a back side of a circuit board 230A, connection electrodes 233*a*, 233*b*, 233*c*, 233*d*, 233*g*, 233*h*, 233*i*, 233*j*, and 233*k* are arranged, mounting lands where electronic components 57 and 58 are mounted are provided.

On an f5 face of a deformed circuit board 240A, a recess 243 is formed, and connection electrodes 245*a*, 245*b*, 245*c*, 245*d*, 245*g*, 245*h*, 245*i*, 245*j*, and 241*k* (not illustrated) are formed to be connected to the respective connection electrodes 233*a*, 233*b*, 233*c*, 233*d*, 233*g*, 233*h*, 233*i*, 233*j*, and 233*k* of the circuit board 230A.

The f9 and f10 of the deformed circuit board 240A have gradients which are close in the optical-axis-direction proximal end side of a semiconductor package 120, and level difference portions S1, S2, and S3 are provided. In addition, connection electrodes 244*a*, 244*b*, 244*c*, 244*d*, 244*g*, 244*h*, 244*i*, 244*j*, and 244*k* are arranged on the entire f9 and f10 faces. In addition, a connection electrode 244*e* is formed in a level difference portion S3 of the f9 face.

The connection electrodes 244*a*, 244*b*, 244*c*, 244*d*, 244*g*, 244*h*, 244*i*, 244*j*, and 244*k* extend from the respective connection electrodes 245*a*, 245*b*, 245*c*, 245*d*, 245*g*, 245*h*, 245*i*, 245*j*, and 245*k* of the f5 face to the f9 or f10 face.

Cables 65*a*, 65*b*, 65*d*, 65*e*, 65*g*, 65*h*, 65*i*, 65*j*, and 65*k* are connected to the connection electrodes 244*a*, 244*b*, 244*d*, 244*e*, 244*g*, 244*h*, 244*i*, 244*j*, and 244*k*, respectively on the level difference portion S2 or S3. Cables 65*c*-1 and 65*c*-2 are connected to the level difference portions S2 and S3 of the connection electrode 244*c*, respectively.

In Modified Example, it is possible to obtain the same effects as those of the fourth embodiment, and it is possible to appropriately select mount positions of the electronic components.

According to some embodiments, because an electronic component is arranged in the immediate vicinity of an image sensor through a circuit board which is close to the image sensor, it is possible to drive the image sensor at a high speed, and to achieve a small diameter of and to obtain a high-quality image.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging unit comprising:
    a semiconductor package having an image sensor and having a connection electrode on a back side thereof;
    a circuit board having connection electrodes on front and back sides thereof, the connection electrode on the front side being in contact with the connection electrode of the semiconductor package;
    a deformed circuit board having at least first, second, and third faces and having connection electrodes on the first, second, and third faces, respectively, a connection electrode of the connection electrodes on the first face being in contact with the connection electrodes of the circuit board;
    an electronic component mounted on the back side of the circuit board; and
    a plurality of cables connected to the connection electrodes on the second and third faces of the deformed circuit board, wherein
    the circuit board has a recess on the back side, or the deformed circuit board has a recess on the first face,
    the electronic component is housed in the recess of the circuit board or in the recess of the deformed circuit board, and
    the circuit board, the deformed circuit board, and the plurality of cables connected to the connection electrodes on the second and third faces are located within a projection plane in an optical axis direction of the semiconductor package.

2. The imaging unit according to claim 1, wherein at least one of the connection electrodes on the second and third faces has a groove shape so as to house a conductor of one of the cables.

3. The imaging unit according to claim 1, wherein the second and third faces of the deformed circuit board face opposite directions,
    the second and third faces have step portions which are close to each other on a proximal end side in the optical axis direction of the image sensor, and
    the connection electrodes are formed on the step portions, respectively.

4. The imaging unit according to claim 3, wherein the connection electrodes are disposed in a staggered arrangement, and
    among the plurality of cables, a cable having a large outer diameter is connected to one of the connection electrodes that is provided on the proximal end side in the optical axis direction.

5. The imaging unit according to claim 3, wherein groove portions are formed on the second and third faces in forward and backward directions of the optical axis direction between the connection electrodes.

6. The imaging unit according to claim 1, wherein the second and third faces of the deformed circuit board face opposite directions, and the second and third faces have gradients such that the second and third faces are close to each other on a proximal end side in the optical axis direction of the image sensor.

7. The imaging unit according to claim 6, wherein level difference portions are provided on the second and third faces, and
    the connection electrodes are arranged in the level difference portions.

8. The imaging unit according to claim 1, wherein the electronic component is housed in the recess on the first face of the deformed circuit board, and
    a part of the connection electrodes on the second and third faces is formed at a position overlapping with the recess in the optical axis direction.

9. The imaging unit according to claim 1, wherein the electronic component is mounted in the recess on the back side of the circuit board, and
    the connection electrodes are formed on a surface except for the recess on the back side of the circuit board.

10. The imaging unit according to claim 1, wherein within a projection area in the optical axis direction of a mounting land on which the electronic component is mounted, a via for connecting at least a part of the connection electrode of the semiconductor package and the connection electrode on the front side of the circuit board to the mounting land on the back side of the circuit board is arranged.

11. An imaging module comprising:
    a semiconductor package having an image sensor and having a connection electrode on a back side thereof;
    a circuit board having connection electrodes on front and back sides thereof, the connection electrode on the front side being in contact with the connection electrode of the semiconductor package;
    a deformed circuit board having at least first, second, and third faces and having connection electrodes on the first, second, and third faces, respectively, a connection electrode of the connection electrodes on the first face being in contact with the connection electrodes of the circuit board, a plurality of cables being connected to the connection electrodes on the second and third faces; and
    an electronic component mounted on the back side of the circuit board, wherein
    the circuit board has a recess on the back side, or the deformed circuit board has a recess on the first face,
    the electronic component is housed in the recess of the circuit board or in the recess of the deformed circuit board, and
    the circuit board and the deformed circuit board are located within a projection plane in an optical axis direction of the semiconductor package.

12. An endoscope system comprising an insertion unit in which the imaging unit according to claim 1 is provided at a distal end of the insertion unit.

* * * * *